(12) United States Patent
Carpenter et al.

(10) Patent No.: US 6,601,006 B2
(45) Date of Patent: Jul. 29, 2003

(54) METHODS FOR THE CALIBRATION OF ANALYTE ASSAYS

(75) Inventors: Charles R. Carpenter, Scarborough, ME (US); Diana N. Sands, Bath, ME (US); Karen E. Plante, Limington, ME (US); Brent M. Nelson, Westbrook, ME (US)

(73) Assignee: Idexx Laboratories, Inc., Westbrook, ME (US)

( * ) Notice: Subject to any disclaimer, the term of this patent is extended or adjusted under 35 U.S.C. 154(b) by 179 days.

(21) Appl. No.: 09/746,821

(22) Filed: Dec. 22, 2000

(65) Prior Publication Data

US 2002/0138222 A1 Sep. 26, 2002

(51) Int. Cl.[7] .......................... G01F 25/00; G01N 31/00
(52) U.S. Cl. .............................. 702/104; 702/22; 702/30
(58) Field of Search ............................ 702/22, 23, 24, 702/25, 30, 104, 152, 155–156; 435/5, 6, 7.1, 7.9, 8; 436/172, 518

(56) References Cited

U.S. PATENT DOCUMENTS

| | | | |
|---|---|---|---|
| 4,627,014 A | | 12/1986 | Lo et al. .................... 364/571 |
| 5,801,007 A | * | 9/1998 | Simpson et al. ............... 435/8 |
| 6,159,698 A | * | 12/2000 | Staples et al. .............. 435/7.1 |
| 6,303,325 B1 | * | 10/2001 | Mehta et al. ................ 435/7.5 |

OTHER PUBLICATIONS

Tillyer, Calibration in three Dimensions : Optimizing a two–parameter calibration Technique to Extend the range of an Immunoturbiclimetric urinary albumin Assay into Antigen Excess, Clinical Chemistry, vol. 36, No. 2, 1990.*

Tillyer; *Calibration in Three Dimensions: Optimizing a Two–Parameter Calibration Technique to Extend the Range of an Immunoturbidimetric Urinary Albumin Assay into Antigen Excess;* Clinical Chemistry, vol. 36, No. 2, p. 307–312; Feb. 1990.

* cited by examiner

*Primary Examiner*—Bryan Bui
(74) *Attorney, Agent, or Firm*—Richard J. Warburg; Foley & Lardner

(57) ABSTRACT

The present invention provides methods for the calibration of detection and/or quantification assays for a wide variety of analytes in wet or dry chemistry assay systems. The invention involves the use of a reagent and calibrator, which provide a detectable signal after reacting with the analyte to be assayed for. In preferred embodiments the calibrator is provided in gross excess. A mathematical relationship is provided that relates a reaction measurement of the analyte sample with the reagent and a reaction measurement of the calibrator with the reagent as an equation that defines a three dimensional surface. This relationship may be used to calibrate the detection and/or quantification assay.

62 Claims, 16 Drawing Sheets

- Reaction Slope vs Calibrator Slope vs Dose (mg/dL)
- Gaussian Fit to Data $x'$: x scaled -1 to +1

$y'$: ln(y) scaled -1 to +1

$T_n(x') = \cos(n * \cos^{-1}(x'))$ $z = a + bT_1(x') + cT_1(y')$
$+ dT_2(x') + eT_1(x')T_1(y') + fT_2(y')$
$+ gT_3(x') + hT_2(x')T_1(y') + iT_1(x')T_2(y') + jT_3(y')$
$+ kT_4(x') + lT_3(x')T_1(y') + mT_2(x')T_2(y') + nT_1(x')T_3(y') + oT_4(y')$
$+ pT_5(x') + qT_4(x')T_1(y') + rT_3(x')T_2(y') + sT_2(x')T_3(y') + tT_1(x')T_4(y') + uT_5(y')$
$+ vT_6(x') + aaT_5(x')T_1(y') + abT_4(x')T_2(y') + acT_3(x')T_3(y') + adT_2(x')T_4(y') + aeT_1(x')T_5(y') + afT_6(y')$

FIG. 16

| 83 mg/dL 37°C | | |
|---|---|---|
| REGEANT DILUTION | SAMPLE SLOPE | CAL SLOPE |
| 0.5X | MEAN = 3.764<br>SD = 0.187<br>%CV = 4.97%<br>AVG R^2 = 0.9993 | MEAN = 6.510<br>SD = 0.195<br>%CV = 3.00%<br>AVG R^2 = 0.9995 |
| 0.75X | MEAN = 5.946<br>SD = 0.177<br>%CV = 2.97%<br>AVG R^2 = 0.9994 | MEAN = 11.071<br>SD = 0.525<br>%CV = 4.74%<br>AVG R^2 = 0.9995 |
| 1X | MEAN = 7.319<br>SD = 0.166<br>%CV = 2.27%<br>AVG R^2 = 0.9995 | MEAN = 15.296<br>SD = 1.264<br>%CV = 8.26%<br>AVG R^2 = 0.9996 |

| 83mg/dL 0.5X37°C | CURVE 1 | CURVE 2 | CURVE 3 | CURVE 4 | CURVE 5 | MEAN | SD | %CV |
|---|---|---|---|---|---|---|---|---|
| Rx | 3.497 | 3.876 | 3.771 | 3.910 | 3.764 | 3.764 | 0.187 | 4.97% |
| Cal | 6.274 | 6.438 | 6.719 | 6.608 | 6.510 | 6.510 | 0.195 | 3.00% |
| Adj Rx | 7.278 | 7.388 | 7.261 | 7.354 | 7.320 | 7.320 | 0.061 | 0.83% |

| EXPECTED VALUE AT 1X | ACTUAL VALUE | % OF DIFF |
|---|---|---|
| 7.319 | 7.320 | 0.02% |

| 83mg/dL 0.75X37°C | CURVE 1 | CURVE 2 | CURVE 3 | CURVE 4 | CURVE 5 | MEAN | SD | %CV |
|---|---|---|---|---|---|---|---|---|
| Rx | 5.998 | 6.141 | 6.049 | 5.691 | 5.854 | 5.946 | 0.177 | 2.97% |
| Cal | 11.285 | 11.113 | 11.807 | 10.686 | 10.466 | 11.071 | 0.525 | 4.74% |
| Adj Rx | 7.297 | 7.459 | 7.186 | 7.235 | 7.421 | 7.320 | 0.118 | 1.61% |

| EXPECTED VALUE AT 1X | ACTUAL VALUE | % OF DIFF |
|---|---|---|
| 7.319 | 7.320 | 0.01% |

FIG. 18-1

| 83mg/dL 0.5X25°C | CURVE 1 | CURVE 2 | CURVE 3 | CURVE 4 | CURVE 5 | MEAN | SD | %CV |
|---|---|---|---|---|---|---|---|---|
| Rx | 2.209 | 2.149 | 2.153 | 2.040 | 2.034 | 2.117 | 0.077 | 3.63% |
| Cal | 3.560 | 3.460 | 3.660 | 3.828 | 3.668 | 3.635 | 0.137 | 3.77% |
| Adj Rx | 7.688 | 7.705 | 7.651 | 7.587 | 7.631 | 7.652 | 0.047 | 0.61% |

| EXPECTED VALUE AT 1X | ACTUAL VALUE | % OF DIFF |
|---|---|---|
| 7.319 | 7.652 | 4.56% |

| REGEANT DILUTION | 83 mg/dL 25°C | | | |
|---|---|---|---|---|
| | SAMPLE SLOPE | | CAL SLOPE | |
| 0.5X | MEAN= 2.117 | | MEAN= 3.635 | |
| | SD= 0.077 | | SD= 0.137 | |
| | %CV= 3.63% | | %CV= 3.77% | |
| | AVG R^2= 0.9992 | | AVG R^2= 0.9991 | |

| REGEANT DILUTION | SAMPLE SLOPE | CAL SLOPE |
|---|---|---|
| 0.5X | MEAN= 6.069<br>SD= 0.077<br>%CV= 1.27%<br>AVG R^2= 0.9995 | MEAN= 6.705<br>SD= 0.262<br>%CV= 3.91%<br>AVG R^2= 0.9995 |
| 0.75X | MEAN= 9.248<br>SD= 0.313<br>%CV= 3.38%<br>AVG R^2= 0.9995 | MEAN= 10.461<br>SD= 0.167<br>%CV= 1.59%<br>AVG R^2= 0.9981 |
| 1X | MEAN= 12.488<br>SD= 0.631<br>%CV= 5.05%<br>AVG R^2= 0.9993 | MEAN= 16.380<br>SD= 3.099<br>%CV= 18.92%<br>AVG R^2= 0.9995 |

| 438mg/dL 0.5X37°C | CURVE 1 | CURVE 2 | CURVE 3 | CURVE 4 | MEAN | SD | %CV |
|---|---|---|---|---|---|---|---|
| Rx | 5.975 | 6.151 | 6.110 | 6.041 | 6.069 | 0.077 | 1.27% |
| Cal | 6.765 | 6.398 | 7.026 | 6.631 | 6.705 | 0.262 | 3.91% |
| Adj Rx | 12.423 | 12.663 | 12.355 | 12.512 | 12.488 | 0.133 | 1.06% |

| EXPECTED VALUE AT 1X | ACTUAL VALUE | % OF DIFF |
|---|---|---|
| 12.488 | 12.488 | 0.00% |

| 438mg/dL 0.75X37°C | CURVE 1 | CURVE 2 | CURVE 3 | CURVE 4 | MEAN | SD | %CV |
|---|---|---|---|---|---|---|---|
| Rx | 9.602 | 9.009 | 9.132 | 9.248 | 9.248 | 0.313 | 3.38% |
| Cal | 10.481 | 10.285 | 10.617 | 10.461 | 10.461 | 0.167 | 1.59% |
| Adj Rx | 12.729 | 12.406 | 12.335 | 12.490 | 12.488 | 0.210 | 1.68% |

| EXPECTED VALUE AT 1X | ACTUAL VALUE | % OF DIFF |
|---|---|---|
| 12.488 | 12.490 | 0.01% |

METHODS FOR THE CALIBRATION OF ANALYTE ASSAYS

The present invention provides methods for the calibration of detection and/or quantification assays of a wide range of analytes.

BACKGROUND OF THE INVENTION

All in vitro diagnostic assays require calibration in order to accurately determine the analyte level of samples or specimens. This has usually been accomplished by generating a standard curve from the measurement of samples of known value. Specimens with unknown levels of analyte can then be measured and compared to the standard curve using mathematically derived relationships. The standard curve may be determined prior to or concurrently with analysis of the sample specimens, depending on the stability and reproducibility of the assay. Methods producing results that vary considerably from assay to assay require that standardization be determined concurrently with each assay. This is undesirable as it increases both cost and time. Assay methods that allow the use of previously determined standards, such as a stored standard curve, and that do not require standardization with each assay would be preferable.

In cases where assay results vary considerably from one assay to the next or over time, the simultaneous measurement of a standard sample of known value with the unknown sample may allow adjustment of standard curves and calculation of accurate results. This method, however, requires that the concurrently run standard be stable over the shelf life of the assay and be measured in the assay method identically to the unknown sample. In dried assay method systems this requirement may be extremely difficult to achieve. It would therefore be desirable to be able to deliver an unmeasured and variable amount of calibrator into a dried reagent assay system and be able to use the results, in association with a previously determined standardization algorithm, to accurately predict unknown analyte levels, regardless of assay perturbations.

The present invention is applicable to a wide variety of both wet and dry chemistry assay systems. A particular type of dry chemistry assay system in which the present invention is useful is described in PCT Publication WO 00/58730, published Oct. 5, 2000.

BRIEF DESCRIPTION OF THE DRAWINGS

FIG. 16—Chebyshev X, LnY Bivariate Polynomial Order 6 Surface Equation.

FIG. 18—Table showing dried reagent calibration system adjustment of sample results with varying temperature and analyte level. Glucose calibrator concentration equals 598 mg/dL.

SUMMARY OF THE INVENTION

The present invention provides methods for the calibration of detection and/or quantification assays for a wide variety of analytes. The assay system to be calibrated may be a dry or wet chemistry assay system. In one embodiment, the analyte may be glucose, but the present invention may be applied to any of a large number of other analytes. The methods allow for the simultaneous performance and calibration of the assays.

In a preferred embodiment, the assay system of the present invention may comprise at least three chemical reactants: 1) an analyte sample of unknown concentration, 2) a calibrator, which may be the analyte or an analyte analog provided in excess or gross excess, and 3) a reagent that may react with the analyte or its analog when present. In one embodiment, the analyte to be assayed for may be glucose, the calibrator may be glucose or a glucose analog provided in gross excess, and the reagent may be glucose Trinder reagent.

The present methods may therefore involve the use of a calibrator, which may be the same chemical as the analyte to be assayed for provided at a concentration in excess or gross excess to the analyte concentration of the assay sample. The calibrator may therefore be delivered into an assay system for an analyte in imprecise or variable amounts without affecting the accuracy of the result obtained.

The assay result may be examined with reference to an algorithm, which adjusts the measured value of analyte concentration to compensate for errors and variations introduced by perturbations in the assay system. The methods of the present invention therefore enable the user to accurately determine analyte concentrations in samples regardless of common assay perturbations. The present invention was arrived at after it was discovered that there exists a mathematical relationship between the slope of the line defining the reaction rate of the analyte with a reagent, and the slope of the line defining the reaction rate of the calibrator with the reagent.

Figure 1:
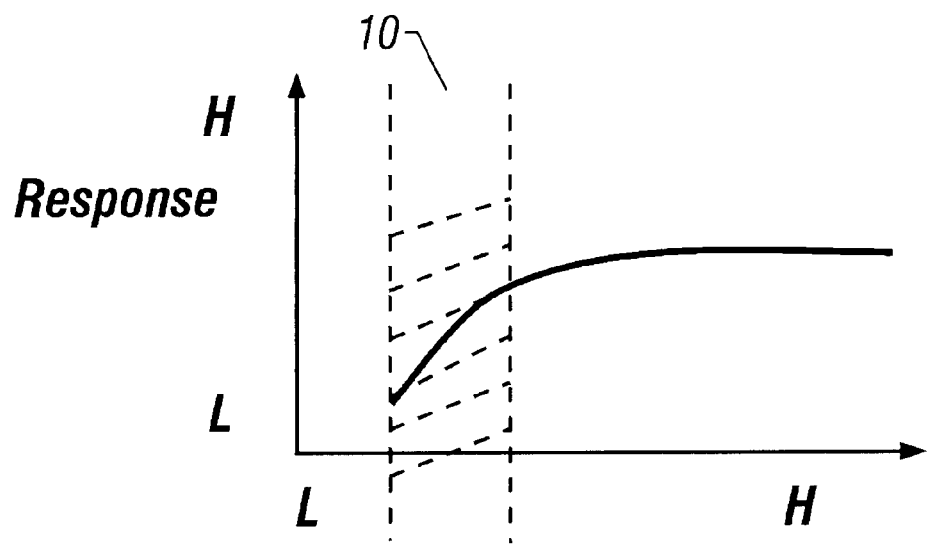
FIG. 1—Reagent Titration Curve, showing the region of interest 10.
Figure 2:
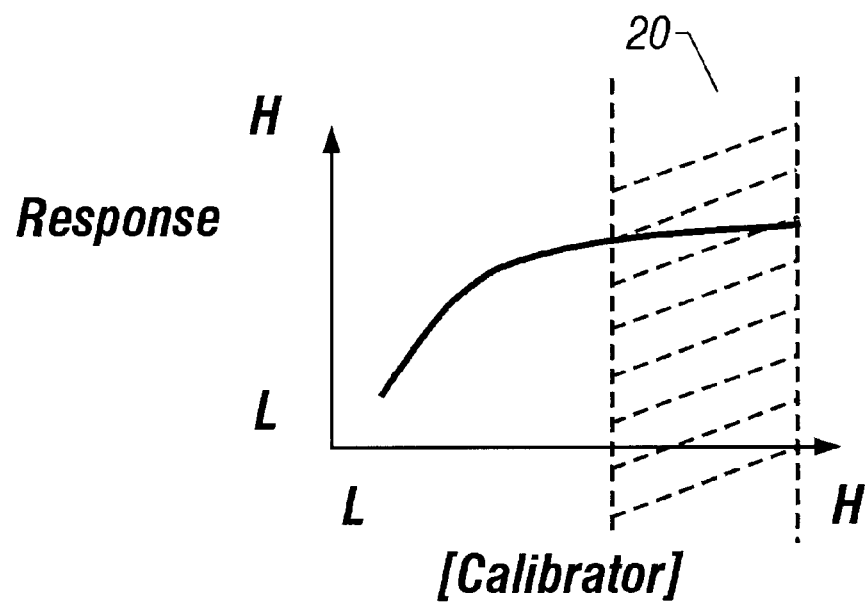
FIG. 2—Analyte Dose Response Curve, showing the region of interest 20.

Referring to FIGS. 1 and 2, the calibration methods of the present invention may utilize reagent at a concentration that is not in gross excess to the calibrator, and therefore dilution and/or degradation of reagent nevertheless leads to a usable diminished reaction. FIGS. 1 and 2 may be used to determine what concentration of calibrator and reagent to use.

Figure 15:
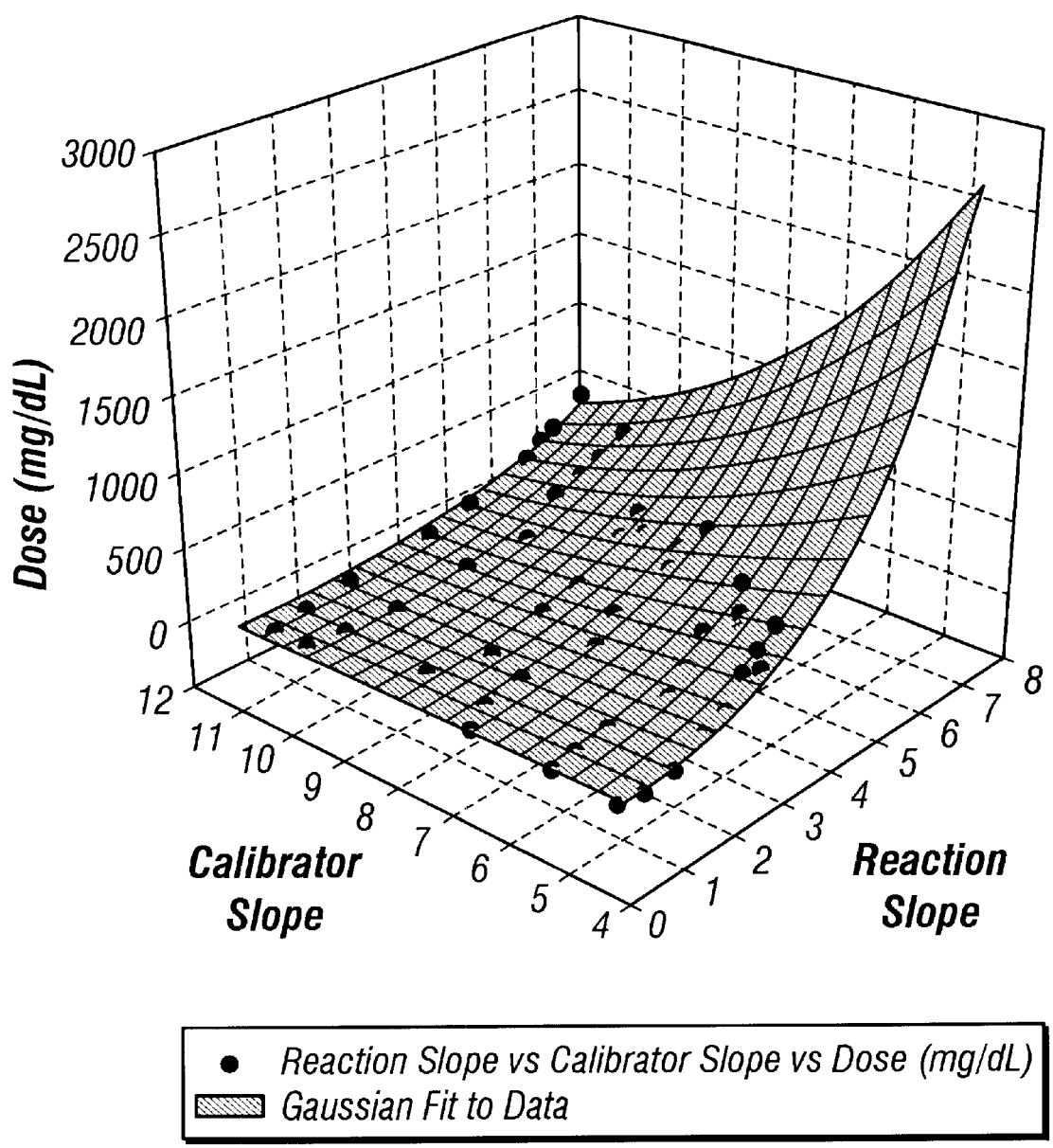
FIG. 15—Three-dimensional Analyte Response Surface. A Chebyshev X, LnY Bivariate Polynomial Order 6.

In the methods of the present invention, any variations in calibrator concentration in the assay due to differences in delivery of calibrator to the reaction and/or due to degradation of calibrator during the life of the reaction product will have no meaningful effect on the results of the assay due to the excess of calibrator used. Other factors affecting the measurement of analyte concentration such as perturbations introduced by time, concentration of reagent, and temperature may therefore have a similar effect on both calibrator and analyte sample, and therefore do not disturb the accuracy of the assay result. The calibrator and the analyte sample may be assayed simultaneously or in sequence. The present inventors discovered unexpectedly that when the invention is practiced as described herein, a unique and definable mathematical relationship exists between the assay results of the calibrator and those of the unknown analyte sample. This relationship may be expressed as a three dimensional surface, as illustrated in FIG. 15. The mathematical equation of this surface may therefore be used to calculate the analyte concentration in the sample based on a measured analyte sample concentration.

Figure 3:
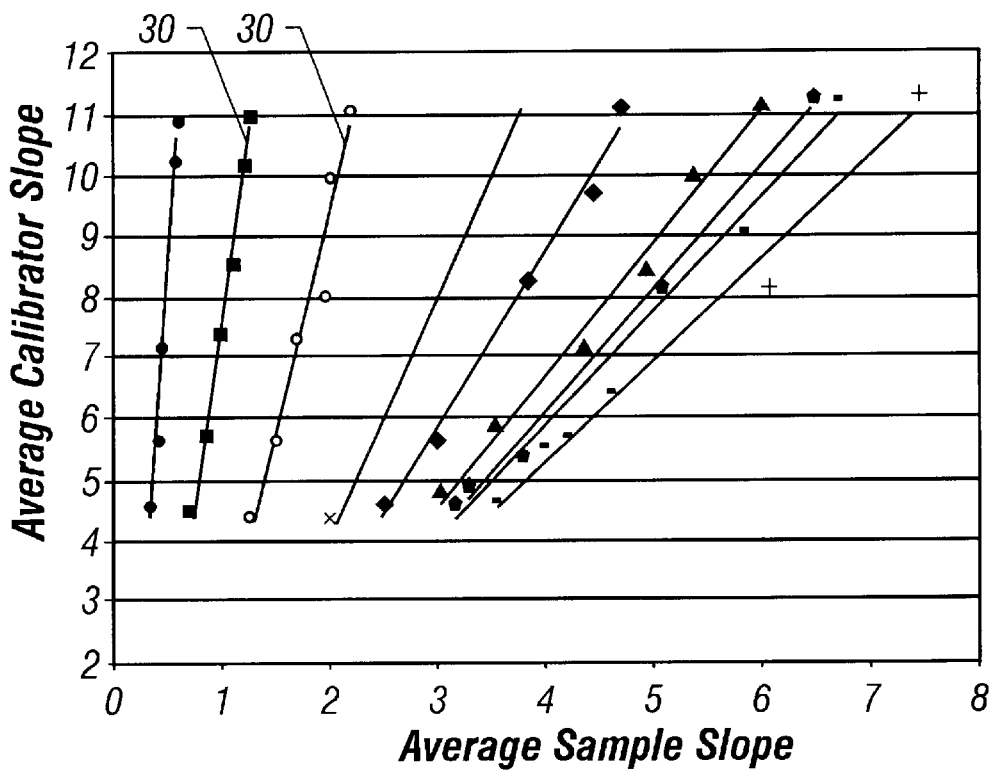
FIG. 3—Glucose Calibration Fan

The relationship may also be expressed as a "calibration fan," as illustrated in FIG. 3. A "fan spine" 30 is one of the lines of the calibration fan.

When calibrator and sample are assayed simultaneously, calibrator results (such as slope in a rate reaction) and analyte sample results define a unique response that is dependent on both reaction measurements. Since the calibrator is in excess, any variation in calibrator reaction rate is due solely to changes in reagent concentration and/or variation in the assay and not to changes in calibrator concentration. Each analyte level may thus be represented by a set of (x,y) points obtained from the assay results of the calibrator and analyte samples. The assay result (expressed as analyte concentration) is thus accurately obtainable even though the assay conditions, reagent potency, and calibrator concentration may vary considerably.

Referring to FIG. 3 when a calibration fan is used, each analyte concentration may be defined by sets of points representing the slopes of the calibrator reaction rates v. the slopes of the analyte reaction rates, each point on the fan spine representing a different reagent concentration. These sets of points therefore define the same value, i.e., they define the slope of a line on the calibration fan corresponding to a particular analyte concentration. The present invention is therefore a unique system of performing assay calibration.

In another aspect the present invention comprises methods for the calibration of detection and/or quantification assays for analytes. The methods may comprise providing a reagent that provides a detectable signal after reacting with the analyte to be assayed for, wherien the reagent also provides a detectable signal after reacting with a calibrator, contacting the reagent with the calibrator and the analyte sample, mathematically relating a reaction measurement of the analyte sample with the reagent and a reaction measurement of the calibrator with the reagent as an equation defining a three-dimensional surface, and utilizing the mathematical relationship to calibrate the detection and/or quantification assay. The reaction measurements of the calibrator and analytes may be the slopes of the lines defining their respective reaction rates. The calibrator may be provided in excess, or even gross excess, to the analyte, and the assays may be performed simultaneously, or in sequence. For example, the calibrator may be provided in a concentration of at least 10 times that of the analyte. But the person of ordinary skill in the art will realize that the amount of calibrator to be used will be dependent on the needs of the particular assay. Different analyte assays may require very different amounts of calibrator. But the person of ordinary skill will realize what amount of calibrator is appropriate by referring to the region of interest on FIG. 2.

The mathematical relationship utilized in the analyte assays of the present invention may be an algorithm. Relationships such as a fourier series bivariate, cosine series bivariate, sigmoid series bivariate, Chebyshev x,y bivariate polynomial, Chebyshev X, LnY bivariate polynomial, Chebyshev LnX, Y bivariate polynomial, Chebyshev LnX, LnY bivariate polynomial, Taylor series rational, and Chebyshev series rational may be utilized when appropriate. When the relationship is a Chebyshev X, LnY bivariate polynomial, it may be an Order 6 equation.

The present invention also involves a method of calibrating a detection and/or quantification assay for an analyte comprising providing a sample of the analyte to be assayed for, a calibrator, and a reagent that provides a detectable signal after reacting with the analyte to be assayed for; determining the slope of the line defining the reaction rate of the analyte to be assayed for with the reagent and the slope of the line defining the reaction rate of the calibrator with the reagent; constructing a calibration fan from the slopes of the lines defining the reaction rates of the analyte or analyte analog to be assayed for and the calibrator, respectively; measuring the apparent value of the analyte concentration, providing a mathematical relationship between the slopes of the lines defining the reaction rates of the analyte or analyte analog and the calibrator; and utilizing the mathematical relationship to determine the concentration of analyte in the sample.

DETAILED DESCRIPTION OF THE INVENTION

By "reagent" is meant one or more chemical entities that provide a detectable signal when reacted with an analyte (or its analog) to be assayed for. The reagent may directly provide the detectable signal, or may provide it at some time after reacting with the analyte or its analog (e.g., through an intermediate molecule).

By "gross excess of calibrator" is meant an amount of calibrator sufficient so that there is no meaningful effect on the assay result with variations in analyte concentration that occur under ordinary assay conditions. Persons of ordinary skill in the art will understand that the amount constituting a "gross excess" may be highly variable depending on the particular reagent being used, analyte being assayed, or assay type. FIG. 2 graphically describes the calibrator concentrations that are in "gross excess" in the region of interest noted thereon. Persons of ordinary skill in the art will readily understand what amount constitutes a "gross excess" in a particular embodiment with reference to FIG. 2.

By "calibration" is meant the derivation of an assay result from an experimentally measured value to arrive at an assay result that has a statistically meaningful relationship to the true value. For example, when the value represents a concentration of an analyte in an assayed solution, calibration will result in a value that has a statistically meaningful relationship to the true concentration of the analyte in the assayed solution. Calibration may apply to one or more measured values.

By "slope of calibrator reaction rate" or "calibrator slope" or "slope of calibrator" is meant the slope of the line representing the reaction rate of the calibrator with the reagent. For example, the slope of the line of a signal generated v. time may yield this line.

By "slope of analyte reaction rate" or "analyte slope" or "slope of analyte" is meant the slope of the line representing the reaction rate of the analyte with the reagent. For example, the slope of the line of a signal generated v. time may yield this line.

A "response curve" may be created by graphically plotting the signal generated by a particular reaction v. time.

By "fan slope" is meant the slope of a fan spine on a calibration fan.

Figure 4:
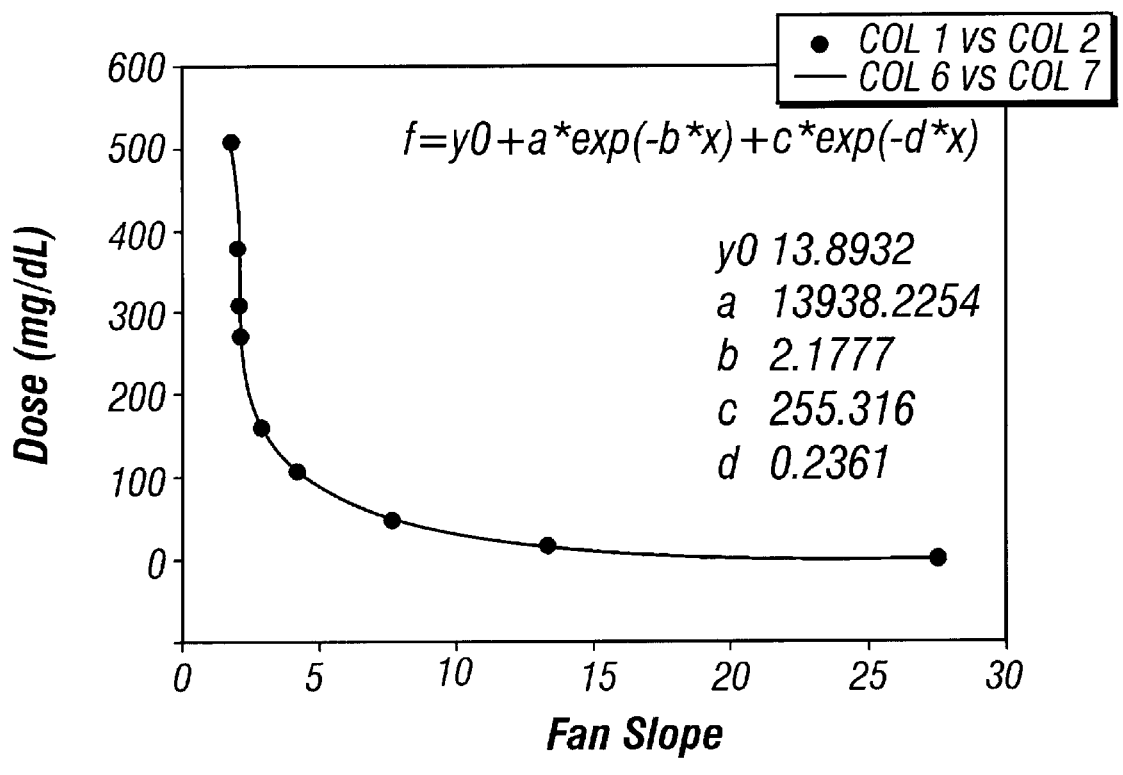
FIG. 4—Analyte Concentration v. Glucose Fan Slope.

An "analyte fan curve" for a particular analyte may be created by graphically plotting the concentrations of known analyte levels v. the slopes of the fan spines on the calibration fan. An example is depicted in FIG. 4.

The "known analyte samples" are samples for which the concentration of the analyte of interest is known. These samples may be used to construct "standard curves" or "calibration fans."

By "true concentration" or "true value" is meant that concentration of analyte that is, in fact, present in the sample.

In preferred embodiments, the present invention may be practiced by determining the mathematical relationship between reaction measurements, and expressing that relationship as a three dimensional surface. This relationship is then used to calibrate the assay and determine the presence or concentration of analyte in the assay solution.

In another embodiment and referring to FIG. 3, a calibration fan may be generated by measuring the slopes of the lines defining the reaction rates of the known analyte samples and the calibrator, and plotting the points. Calibration fans may also be generated from any other reaction rate measurement. In preferred embodiments, a calibration fan may be generated by plotting the slope of the line representing the reaction rate of the known analyte sample v. the slope of the line representing the reaction rate of the calibrator, i.e., the slopes of the response curves. This may be done at the same known analyte concentration but at different reagent concentrations, resulting in a set of points, each point representing a coordinate on the same "fan spine," indicated by 30 on FIG. 3. One therefore generates a set of points defining the same value, i.e., the points define the slope of a particular line on the calibration fan, the slope of which corresponds to a particular analyte concentration. Each point on the fan spine represents a distinct reagent concentration in the assay.

The concentration of analyte in a sample may therefore be determined by identifying the intersection of the slope of the reaction rate for the unknown analyte sample and the slope of the reaction rate of the calibrator, as depicted on a calibration fan. Each unique intercept point on the calibration fan defines only one possible concentration of analyte. Thus, by utilizing a mathematical relationship between the slopes of the reaction rates of the analyte sample and calibrator, the fan spine may be defined and its slope determined. Without being bound by any particular theory, it is believed that many factors that affect the assay results do so in a manner generally equivalent to the way reagent concentration affects assay results. Thus, the slope of each fan spine corresponds to a particular analyte concentration. In this manner, an analyte fan curve may be created, such as that depicted in FIG. 4.

Mathematical Relationships

In a preferred embodiment, the slopes of the reaction rates of the calibrator and sample analyte, and the slope of the reaction rate of the known analyte concentration, may define a three-dimensional surface. The equation defining this surface allows the determination of analyte concentration in a sample. The surface may be generated by utilizing the measured calibrator slope and measured analyte sample slope, and plotting against the known analyte concentration (FIG. 15). One may therefore determine the analyte concentration of a sample using this relationship. A statistically significant surface equation may be generated by using commercially available analysis tools, such as TableCurve 3D™ (SPSS Inc., Chicago, Ill.) or another three-dimensional graphing program that does surface regression. One may therefore determine the unknown analyte concentration using this relationship.

Surface Analysis from Empirical Data

Figure 17:
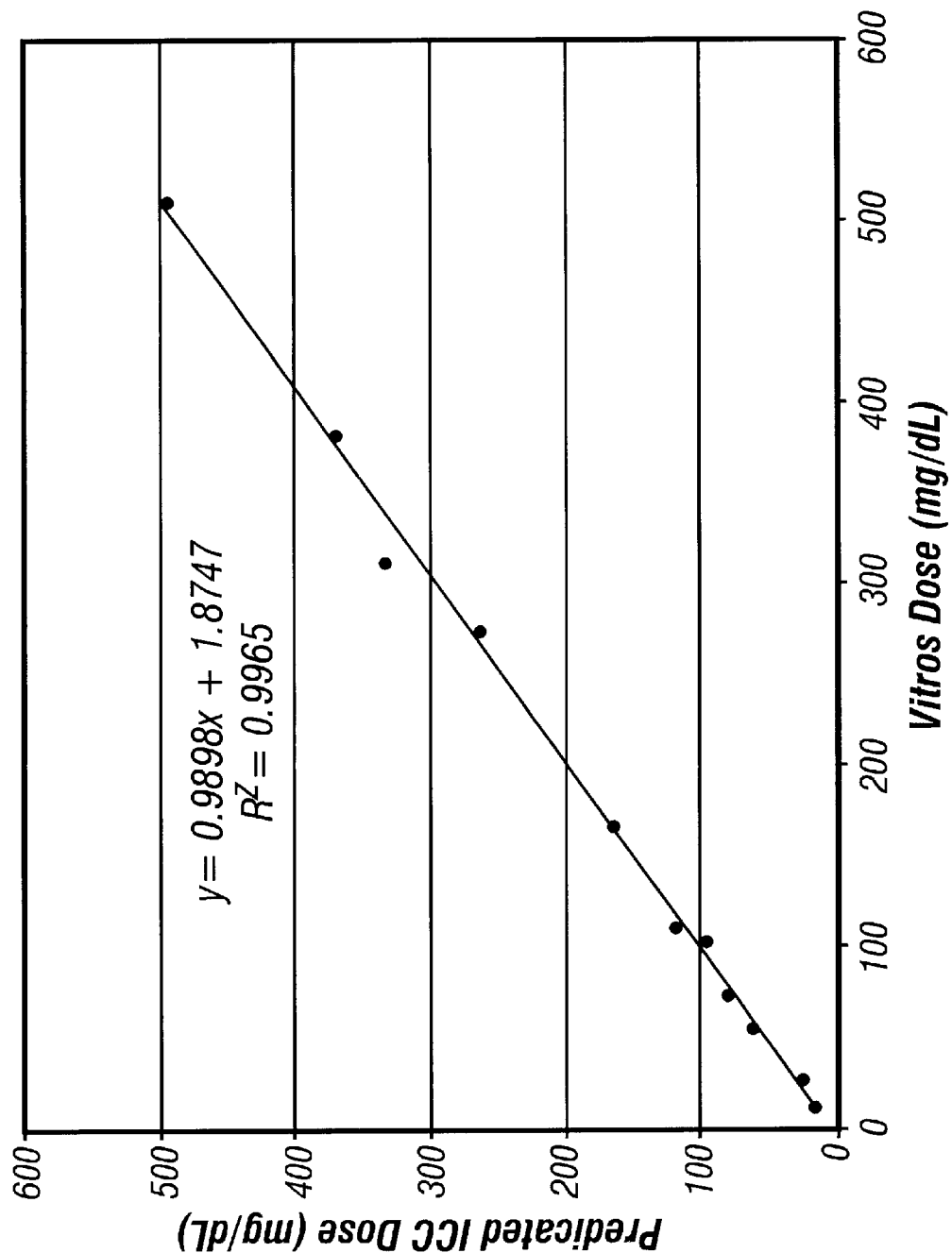
FIG. 17—Glucose ICC v. Vitros Correlation Curve (Chebyshev X, LnY Bivariate Polynomial Order 6). The diamonds show the predicted concentration according to the present invention, and the linear correlation with the Vitros system.

Referring to FIGS. 15–17 and using glucose as an example, a surface may be defined by using a Chebyshev X, LnY Bivariate Polynomial Order 6 equation. The Chebyshev solutions of analyte concentration according to the present invention are seen to correlate with those of the Vitros™ system assay (Ortho Diagnostics, Raritan, N.J.), as shown in FIG. 17.

To calculate the concentration of an unknown analyte using the Chebyshev surface, one must transform the analyte sample slope and calibrator sample slope into values to be used in the Chebyshev formula. The highest x value ($x_{max}$) will transform to an x' value of 1 and the lowest x value ($x_{min}$) will transform to x'=−1. Similarly the highest ln(y) value ($y_{max}$) will transform to y'=1 and the lowest ln(y) value ($y_{min}$) will become y'=−1. The transformations and formula for the Chebyshev X, LnY Bivariate Polynomial Order 6 surface follows are illustrated in FIG. 16, where values a through v and aa through af are constants determined from the surface analysis. The scaling factors for calculating unknowns and transforming them into x' and y' values usable in the surface equation are constant relationships determined from the empirical data.

Calculate Unknowns:

From the values $x_{min}$=minimum analyte sample slope, $x_{max}$=maximum analyte sample slope and $x_{range}$=($x_{max}$−$x_{min}$)/2 from the surface empirical data, the scaling factor for an analyte slope for an unknown sample $x_m$ is:

$$x' = \left( \frac{x_m - (x_{\min} + x_{range})}{x_{range}} \right) \quad \text{Equation 1}$$

where $x_m$ is the measured value of the analyte sample slope.

A similar relationship can be found for y' except the values for y are first transformed by the function ln(y), where y>0.

From the values $y_{min}$ natural log (ln) of minimum calibrator slope (ln(y)), $y_{max}$=ln of maximum calibrator slope (ln(y)) and $y_{range}$=($y_{max}$−$y_{min}$)/2 from the surface equation, the scaling factor for a measured calibrator slope $y_m$ is:

$$y' = \left( \frac{\ln(y_m) - (y_{\min} + y_{range})}{y_{range}} \right) \quad \text{Equation 2}$$

where $y_m$ is the measured value of the calibrator slope.

To calculate values for $T_n(x')$, Equation 3 is used:

Equation 3

$$T_n(x')=\cos(n*\cos^{-1}(x'))$$

EXAMPLES

For $T_4(x')$ the value for n=4 so the function yields $\cos(4*\cos^{-1}(x'))$.

For $T_3(Y')$ the value for n=3 so the function yields $\cos(3*\cos^{-1}(y'))$.

From these values, the analyte concentration (z) can be calculated from the surface equation.

Example for Glucose

Using the method of the present invention to determine the concentration of glucose in a sample of canine blood, an analyte sample slope was calculated to be 1.334 and a simultaneously measured calibrator slope was determined to be 5.687.

For a previously calculated Chebyshev X, LnY Bivariate Polynomial Order 6 surface for glucose using empirical data, values for the scaling constants are found in Table 1:

TABLE 1

| | Scaling Constants | | |
|---|---|---|---|
| $X_{min}$ | $X_{range}$ | $y_{min}$ | $y_{range}$ |
| 0.35 | 3.49 | 1.49 | 0.472 |

Using equation 2 and 3 to scale the analyte sample slope, the values for x' and y' become:

$$x' = \left(\frac{1.334 - (0.35 + 3.49)}{3.49}\right) = -0.72$$

$$y' = \left(\frac{\ln(5.687) - (1.49 + 0.472)}{0.472}\right) = -0.47$$

The next step is to calculate the $T_n(x')$ values for each n from 1 to 6, see Table 2:

TABLE 2

| $T_n(x')$ calculation for n = 1 to 6 | | | | | | | | | | | |
|---|---|---|---|---|---|---|---|---|---|---|---|
| $T_1(x')$ | $T_2(x')$ | $T_3(x')$ | $T_4(x')$ | $T_5(x')$ | $T_6(x')$ | $T_1(y')$ | $T_2(y')$ | $T_3(y')$ | $T_4(y')$ | $T_5(y')$ | $T_6(y')$ |
| −0.72 | 0.03 | 0.67 | −1.00 | 0.76 | −0.09 | −0.47 | −0.56 | 0.99 | −0.36 | −0.66 | 0.97 |

Table 3 shows all the coefficients for the Chebyshev surface:

TABLE 3

| Coefficients of Chebyshev surface equation | |
|---|---|
| a | 1292.255 |
| b | 1982.974 |
| c | −1713.311 |
| d | 924.1095 |
| e | −2731.559 |
| f | 826.3733 |
| g | 221.3207 |
| h | −1360.288 |
| i | 1338.078 |
| j | −267.4519 |

TABLE 3-continued

| Coefficients of Chebyshev surface equation | |
|---|---|
| k | −22.47744 |
| l | −345.0376 |
| m | 695.1403 |
| n | −430.1756 |
| o | 50.69698 |
| p | −30.8945 |
| q | 18.29384 |
| r | 198.8207 |
| s | −210.0898 |
| t | 81.72447 |
| u | −10.11554 |
| v | −2.686572 |
| aa | 30.12252 |
| ab | 18.22181 |
| ac | −55.72533 |
| ad | 29.35387 |
| ae | −18.73479 |
| af | −3.657788 |

By plugging the values from Table 2 and Table 3 into the equation depicted in FIG. 16, the glucose analyte concentration is calculated to be 48.2 mg/dL. The Vitros™ system value for this sample was determined to be 48 mg/dL, yielding a percent difference of 0.42% between the two methods.

As mentioned, surface analysis (the Chebyshev equations) is not the only manner in which the analyte concentrations can be determined. For example, analyte concentrations can also be determined according to the following manner.

Calibrator Fan Generation

The present invention may also be practiced without generation of a three dimensional surface. For any consistent reaction rate measurement a calibration fan can be generated by measuring the reaction rates of the known analyte and calibrator samples. As noted, a calibration fan can also be generated from any other reaction rate measurement. FIG. 3 provides an example of a type of calibration fan that may be generated. When each set of slope values is plotted, each analyte concentration falls on a distinct fan spine. When different reagent concentrations are used, one may obtain different points on the same fan spine for a particular analyte concentration. A fan slope can be determined by measuring the slope of the fan spine.

Determination of Analyte Concentration From a Fan Spine

When an analyte sample of unknown concentration is measured, the analyte concentration can be determined by solving simultaneous equations that use the measured reaction rates of the analyte sample and calibrator, and determining the slope of the fan spine generated from the data collected.

Using a pair of equations that describe different points on the fan spine, a relationship may be generated between the measured reaction rate slope of the unknown analyte sample and a reaction rate slope derived according to the present invention—a derived reaction rate slope. In the embodiment described here for measuring glucose concentrations, the fan spine is linear. The relationships may be described as:

$$y_c = mx_c + b \qquad \text{Equation 4}$$

$$y_m = mx_m + b \qquad \text{Equation 5}$$

where m is the "fan slope" that is interpolated from a fan spine on the calibration fan, b is the "fan intercept" also interpolated from the fan spine, $x_m$ is the measured slope of the reaction rate of a sample of unknown concentration, $y_m$ is the measured calibrator slope, $y_c$ is the standard calibrator slope and $x_c$ is the derived analyte reaction rate slope, i.e., the slope derived according to the present invention.

By subtracting the second equation from the first and rearranging the arguments, the following equation can be derived to calculate reaction slope ($x_c$), which may be used on an analyte fan curve (e.g., FIG. 4):

$$x_c = \frac{(y_c - y_m)}{m} + x_m \qquad \text{Equation 6}$$

Interpolating Slope and Intercept from the Calibration Fan

For each fan spine on a calibration fan, there is a unique slope and intercept for each analyte concentration. Referring to FIG. 4, the relationship between analyte concentration and fan spine slope is an exponential decay type function. A similar relationship exists between analyte concentration and the fan spine intercept.

From the equation for a line, the relationship between the slope and the coordinates can be determined:

$$m = \frac{(y_m - b)}{x_m} \qquad \text{Equation 7}$$

Each measurement of calibrator reaction rate slope and analyte reaction rate slope represents an (x,y) coordinate on a fan spine of the calibration fan. By determining the slope of the unique fan spine that this point falls on, the analyte concentration can be determined from the analyte concentration v. fan slope relationship, an embodiment of which is depicted in FIG. 4.

Utilizing Equation 7, the fan spine slope is determined for each x,y coordinate and the value obtained is compared with a table of known fan slopes and their corresponding x,y coordinates. Through interpolation, the x,y coordinate is used to derive a new equivalent fan slope using the mathematical methods described above. Referring to FIG. 4, this slope is entered into the equation defining the curve of the analyte fan curve and the analyte concentration is thereby determined.

Referring to FIG. 3, the calibrator and analyte slope correlation therefore illustrates the unique relationship between these slopes for each analyte concentration. By knowing both slopes, the analyte concentration can be determined by finding the fan spine upon which the coordinate pair falls. Referring to FIG. 4, the slope of the appropriate fan spine (the "fan slope") is used to identify the corresponding analyte concentration.

The accuracy of the present calibration methods extends over the course of many days and can be applied to a commercially available standard reagent stored under a variety of conditions. Therefore, the present invention eliminates the common requirements of many assays that the reagents be stored under carefully controlled conditions (e.g., storage at 4° C.). In the present invention, Trinder glucose assays were found to produce valid results even when the Trinder reagent was stored at 0.4× at room temperature (22°) or incubated at 37° C. for six days.

The calibration system of the present invention can be applied in a wet or dry chemistry format to determine the concentration of a wide variety of analytes. Using the principles described herein, the invention may be applied to assays for many analytes, including, but not limited to those that here follow. This list is not exhaustive or all-inclusive, as the person of ordinary skill in the art will realize that the methods described herein will be applicable to almost any soluble analyte. Thus, the present invention may be used to simultaneously perform and calibrate detection and/or quantification assays for alanine amino tranferase, albumin, alkaline phosphatase, ammonia, amylase, aspartate amino transferase, total bilirubin, calcium, cholesterol, creatine kinase, creatinine, 2-glutamyl transferase, glucose, lactate dehydrogenase, lipase, magnesium, phosphorus, protein, triglyceride, urea nitrogen, and uric acid.

The present invention may also be useful in the calibration of other types of dry chemistry systems, such as that described in PCT Publication WO 00/58730. For example, the solid phase (or fluid transport material) may be charged with a reagent and the analyte sample and calibrator applied to the solid phase. The analyte sample and calibrator may travel through the solid phase and form a reaction interface with the reagent.

In another embodiment, a diluent may be applied to the solid phase and travel through the solid phase thereby dissolving a reagent charged on the solid phase. The reagent would then form an interface with an analyte sample or calibrator to produce the detectable result.

The analyte sample, calibrator, and reagent may also be applied to the solid phase at separate and distinct points. Any or all of the analyte sample, calibrator and reagent may travel through the solid phase to form one or more reaction interfaces, as suits the needs of the particular assay. For example, the analyte sample and reagent may be applied at separate points on the solid phase and flow towards one another to form a first reaction interface. The calibrator may also be applied at a separate point and flow to form a second reaction interface that is separate and distinct from the first reaction interface.

The solid phase may be constructed of, for example, nitrocellulose that is cast onto a polyvinylchloride or polyester backing material.

Technical Notes

Commercially available reagents may be used in the present invention (e.g., 0.4× dilution for Sigma™ Trinder reagent in a glucose assay). The calibrator system of the present invention can be applied in a wet or dry chemistry format. The following examples illustrate the preparation and use of the invention in a dry chemistry format, such as that disclosed in PCT Publication WO 00/58730. These examples illustrate the calibrator system as it is applied to calibration of a system for determining concentrations of glucose. The parameters and reagents used were those described below unless otherwise stated in the example.

In preferred embodiments, the membranes used may be 1.2 $\mu$m hydrophilic Durapore™ membranes, commercially available from Millipore Corporation (Bedford, Mass.). The membranes may be stored dessicated at room temperature. The glucose reagent used may be any of various commercially available glucose Trinder reagent (e.g., Sigma Chemical Co., St. Louis, Mo.) and was stored at 4 C. Glucose Trinder reagent may comprise a mixture of glucose oxidase, peroxidase, 4 amino anti-pyrine and 3,5-dichloro-2-hydroxy-bezenesulfonic acid.

The effect on interface chemistry of concentration of glucose Trinder reagent was tested by titrating the reagent from 1× up to 10× by simply reconstituting the reagent bottle with deionized water. In final dry chemistry devices, variations in concentration of reactants will occur due to minor fluctuations in elution and chemical stability. Therefore, in preferred embodiments, reagent concentrations may be in excess to compensate for incomplete elution and/or reagent instability.

To maximize the glucose reaction in the calibrator solution, 4-aminoantipyrine (4AP) and 3,5-dichloro-2-hydroxy-benzenesulfonic acid may be added to the Trinder reagent. In a preferred embodiment, these reagents may be added in the amounts of about 2.5 mmol/L 4AP and 100 mmol/L 3.5-dichloro-2-hydroxy-benzenesulfonic acid and the commercially available Trinder reagent may be reconstituted with 20 ml of water (5 times the manufacturer's recommendation). Without wanting to be bound by any particular theory, it is believed these additives increase the amount of leuco dyes present at the interface to achieve maximum reactivity.

The present invention is described herein with reference to the slopes of the reaction rates of the calibrator and unknown analytes. But it is possible to determine the unknown analyte concentration using many other reaction rate measurements. For example, utilizing the same concepts as taught herein, one may determine unknown analyte concentrations by utilizing endpoint analysis, percent of a reactant bound to a solid phase, the count of an assay parameter bound to a solid phase (e.g., radioactivity), optical density, and many other parameters where there is an analyte/calibrator relationship as taught herein. The above list is not all inclusive, but rather is provided by way of example. The person of ordinary skill will be able to identify many other reaction rate measurements to which the present invention may be applied, and they too are within the scope of the present invention.

The following Examples illustrate particular embodiments of the present invention and should not be construed as limiting. The person of ordinary skill will be able to adapt the concepts and principles taught herein to many formats and circumstances.

The samples used in the examples were fetal bovine serum (FBS) based for liquid format calibrations, or were merely glucose in water in the case of dry chemistry format calibrations. The calibrator solution used contained 14,700 mg/dL glucose in fetal bovine serum, although the person of ordinary skill will realize that various concentrations of glucose or other analyte being assayed may be useful, as needs require.

Example 1

This Example will show a general hypothetical generation of a calibration fan and measurement of the unknown concentration of an analyte in a sample (glucose). This Example represents one embodiment of the invention and changes and adaptations as necessary will be apparent to those of ordinary skill in the art.

The assay materials are generated. Samples of glucose of known concentration are generated. These are the known analyte concentration samples. A sample of calibrator is also generated. The calibrator is glucose in gross excess, for example, at 14,700 mg/dl glucose. Glucose Trinder reagent is provided in four different concentrations.

The response curves of the calibrator and the known analyte samples are performed at four different concentrations of Trinder reagent and at different known concentrations of glucose samples. The slopes of the reaction rates for the known analyte and calibrator are calculated at the different concentrations of reagent. The points are plotted on a calibration fan to generate a curve similar to that depicted in FIG. 3. The slopes of the fan spines on the calibration fan generated are also plotted against the known analyte sample concentrations to yield a figure such as that in depicted in FIG. 4 (i.e., an analyte fan curve). The values of the known analyte and calibrator samples may preferably be used to generate a Chebyshev surface, such as that depicted in FIG. 15.

A sample of unknown glucose concentration is now assayed with a calibrator. The response curves of the glucose sample and calibrator reaction rates are generated and the slopes calculated. In the preferred method, the slope of the analyte reaction rate and the slope of the calibrator reaction rate may be entered into the equation that describes FIG. 15 and the analyte concentration is thereby determined. In another embodiment, the slopes of the fan spines from the calibrator fan may be used to generate an analyte fan curve such as that depicted in FIG. 4, and the unknown values determined therefrom.

Example 2

Figure 5:
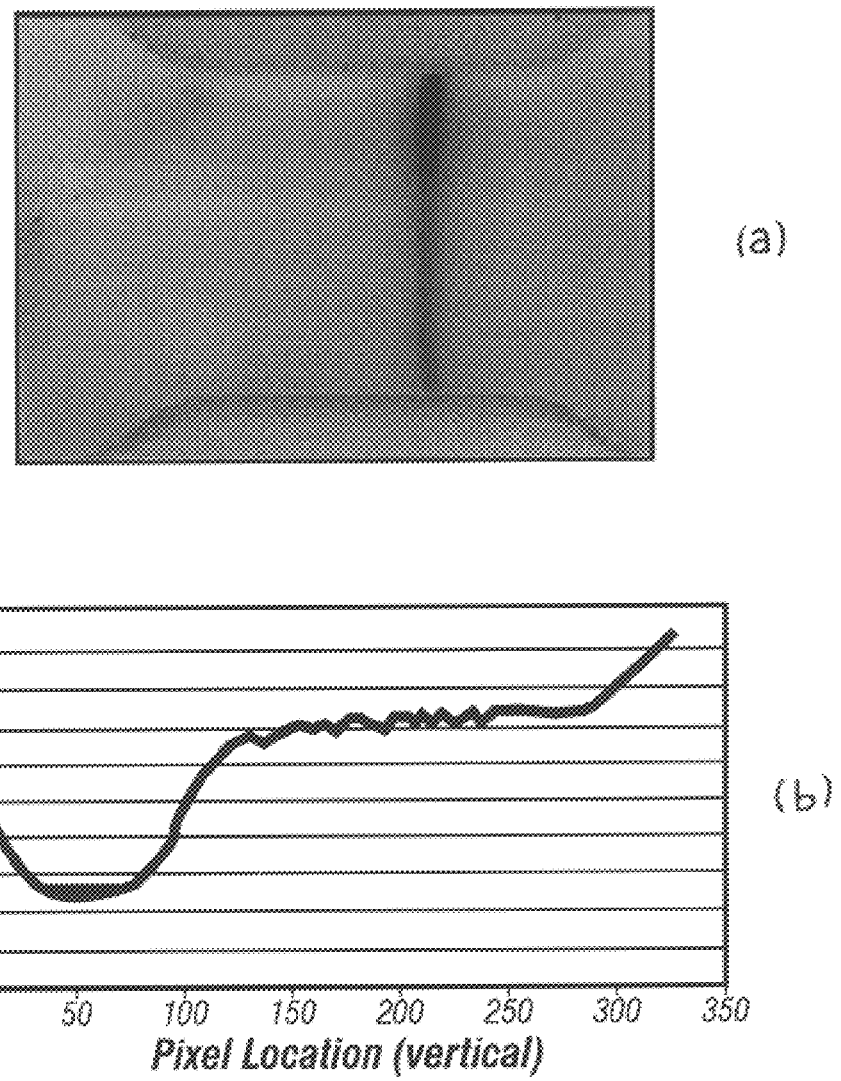
FIG. 5—Dried reagent calibration system assay development. Pixel intensity corresponds to calibrator and sample read areas. The glucose line profile from the top to the bottom of the interface is shown in FIG. 5a, and the pixel location (vertical) in FIG. 5b.

Excess calibrator was applied to the membrane using a Biodot™ ink jet printer. The spotting volume was 90 nL, which consisted of six 15 nL drops applied at about a 0.4 mm pitch. The printed membranes were dried overnight and stored in a vacuum chamber. As shown in FIG. 5, the sample reconstituted the dried calibrator as it passed through the membrane and transported it to the interface as a concentrated front. The interface formed distinctly from the edge of the dried calibrator spot. Since the calibrator and sample traveled the same path to the interface, the conditions that affect the calibrator interface are the same as those for the analyte reaction interface.

Figure 10:
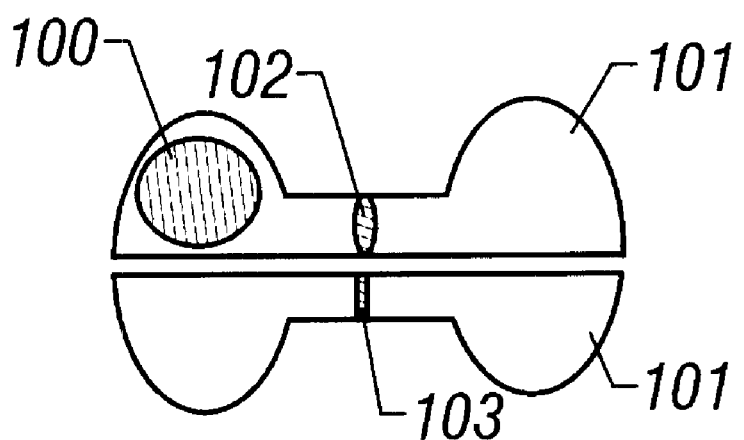
FIG. 10—Dried reagent calibration system with split dogbone.

Excess calibrator was contained within a pad of glass fiber, polyester or nylon media. Pad media was soaked in solutions of excess glucose. Calibrator pads were dried overnight and stored in a vacuum chamber. Pads were positioned onto the device with a slight overlap. Referring to FIG. 10, sample was applied to a precursor pad that simultaneously hydrates both the calibrator pad and the blank sample pad. Reagent traveled from the opposed side of the device and met the calibrator and sample. Reactions proceeded as previously described on a split dogbone format.

Identification of the appropriate read areas within the interface facilitated proper analysis. Referring to FIG. 5, calibrator and analyte sample results were identified within the interface by vertical line profiles, the calibrator being noticeably darker than the analyte sample (since it was used in excess). The line profile indicated pixel intensity within the interface corresponding to interface development. Standard region of interest (ROI) boxes for data analysis (typically 100×100 pixels) may be too large for optimal analysis of the calibrator system ROI boxes for calibrator results may preferably be restricted to 25 vertical pixels by 100 horizontal pixels, while sample ROI boxes are preferably no larger than 50 vertical pixels by 100 horizontal pixels.

Figure 6:
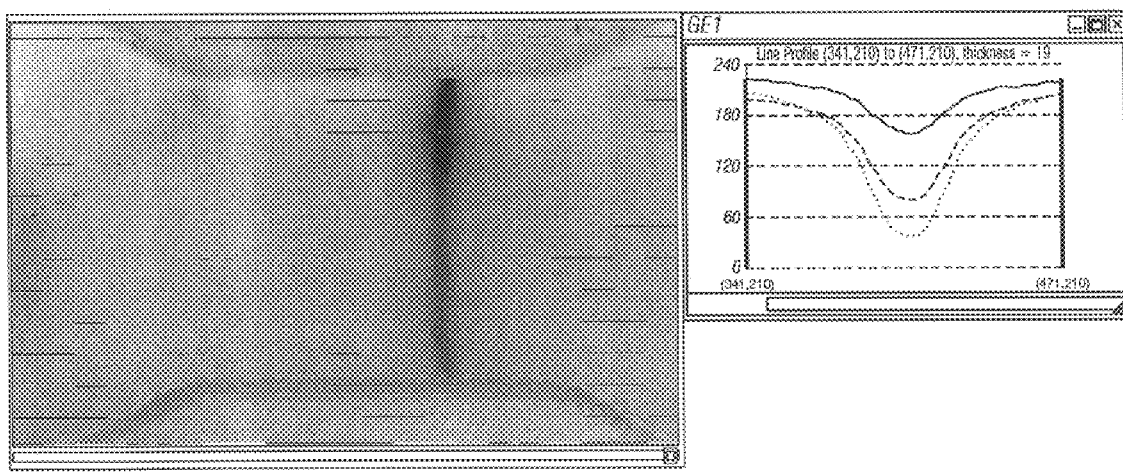
FIG. 6—Dried reagent calibration system simultaneous measurement of calibrator and analyte sample at interface. Glucose sample concentration 71 mg/dL, dried glucose calibrator concentration 910 mg/dL.

Referring to FIG. 6, data reduction methods may more clearly distinguish calibrator reaction rate from analyte sample reaction rate.

Table 4 shows the measured analyte sample reaction rate adjusted to arrive at the analyte concentration in the dried calibrator system according to the present invention. Adjustments were based on the correlation between the two interfaces such that the slope of the analyte reaction rates was used to calculate the concentration of analyte in an unknown sample using a standard reagent value. The reagent was derived from Sigma™ Trinder reagent as described previously and stored at 4° C.

Since the calibrator was used in excess to analyte, the calibrator slope value remained constant regardless of the analyte sample concentration that transferred it to the interface. Measurement of the slopes of the lines defining both the calibrator reaction rate and analyte reaction rate will determine analyte concentration regardless of reagent concentration and other assay conditions (e.g., temperature). The person of ordinary skill in the art will understand that any reaction parameter may be used, and that one is not limited to utilizing only the slopes of the reaction rates, as described in this embodiment.

TABLE 4

Dried reagent calibration system adjustment of sample results. "Dose" refers to analyte concentration.

0.5 × FBS 0.25 × Reagent

|  | Calibrator Slope y1 | Reaction Slope x1 | Adjusted Reaction Slope x0 |
| --- | --- | --- | --- |
| Curve 1 | 3.017 | 0.858 | 3.257 |
| Curve 2 | 3.102 | 0.774 | 3.355 |
| Curve 3 | 3.434 | 0.920 | 3.262 |
| Curve 4 | 3.198 | 0.839 | 3.306 |
| Curve 5 | 3.495 | 1.024 | 3.168 |
| Curve 6 | 3.653 | 1.223 | 2.995 |
| Curve 7 | 3.985 | 0.961 | 3.309 |
| Curve 8 | 3.810 | 0.957 | 3.285 |
| Curve 9 | 3.828 | 0.927 | 3.319 |
| Curve 10 | 3.635 | 1.187 | 3.028 |
| Curve 11 | 3.226 | 0.960 | 3.189 |
| Curve 12 | 2.583 | 0.837 | 3.210 |
|  | Mean | 0.956 | 3.223 |
|  | SD | 0.135 | 0.114 |
|  | % CV | 14.17% | 3.53% |

0.5 × FBS 0.5 × Reagent

|  | Calibrator Slope y1 | Reaction Slope x1 | Adjusted Reaction Slope x0 |
| --- | --- | --- | --- |
| Curve 1 | 6.718 | 1.461 | 3.245 |
| Curve 2 | 7.088 | 1.469 | 3.297 |
| Curve 3 | 6.128 | 1.620 | 2.992 |
| Curve 4 | 7.147 | 1.605 | 3.170 |
| Curve 5 | 7.281 | 1.659 | 3.138 |
| Curve 6 | 7.045 | 1.701 | 3.058 |
| Curve 7 | 6.938 | 1.537 | 3.205 |
| Curve 8 | 7.938 | 1.727 | 3.175 |
| Curve 9 | 6.920 | 1.516 | 3.223 |
| Curve 10 | 6.419 | 1.358 | 3.301 |
|  | Mean | 1.565 | 3.183 |
|  | SD | 0.117 | 0.098 |
|  | % CV | 7.50% | 3.09% |

| 0.5 × FBS 1 × Reagent | 3.198 |
| --- | --- |
| Mean Adj Reaction Slopes | 3.201 |
| St Dev | 0.0216 |
| % CV | 0.67% |

| $y = 6.262 \times -2.683$ | |
| --- | --- |
| a | 6.262 |
| b | 2.683 |
| y0 | 17.388 |

Because variation of the calibrator reaction rate correlates with variation in the analyte sample reaction rate, the system may correct for other variations in the assay. For example, the effects of temperature on system calibration were investigated. Assays were performed at room temperature (approximately 25° C.), and again at 37° C. on a heat block. In Table 2 it is illustrated that the calibrator system correctly adjusted for variations in temperature to arrive at statistically meaningful assay results.

Example 3

This example illustrates the calibrator system of the present invention applied using a liquid calibrator system to determine concentrations of glucose. This system may be useful for further minimizing other factors that may introduce variables into the dried calibrator system (e.g., elution of reagent from the sample pad or membrane, or stability of reagents).

Figure 7:
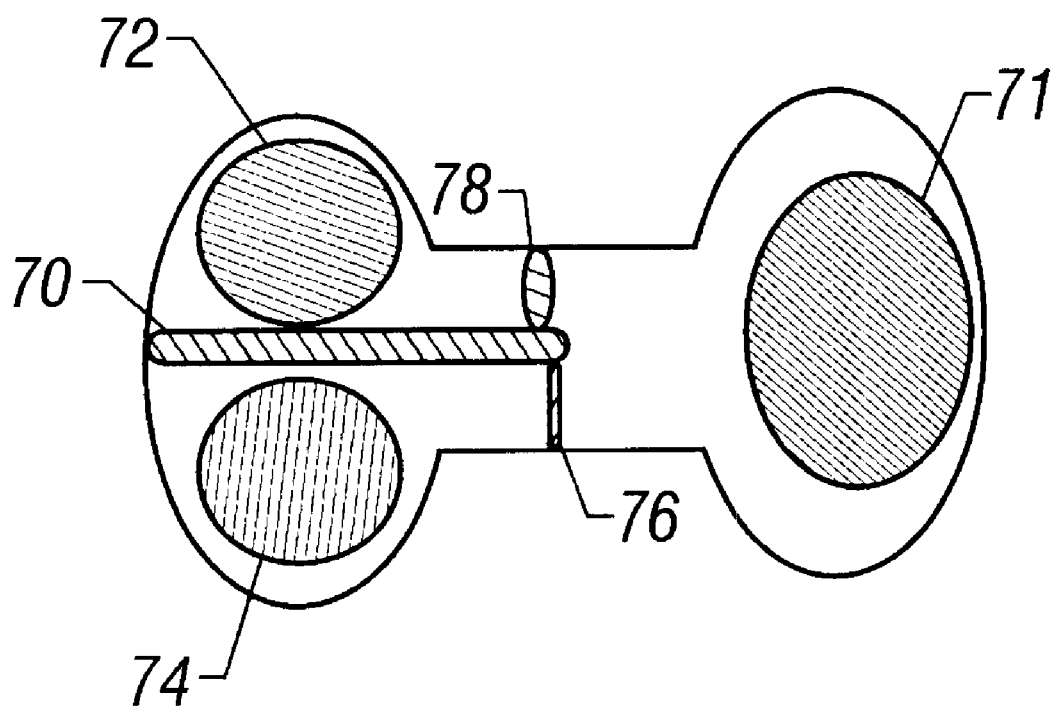
FIG. 7—Liquid reagent calibration system with hydrophobic ink barrier.
Figure 8:
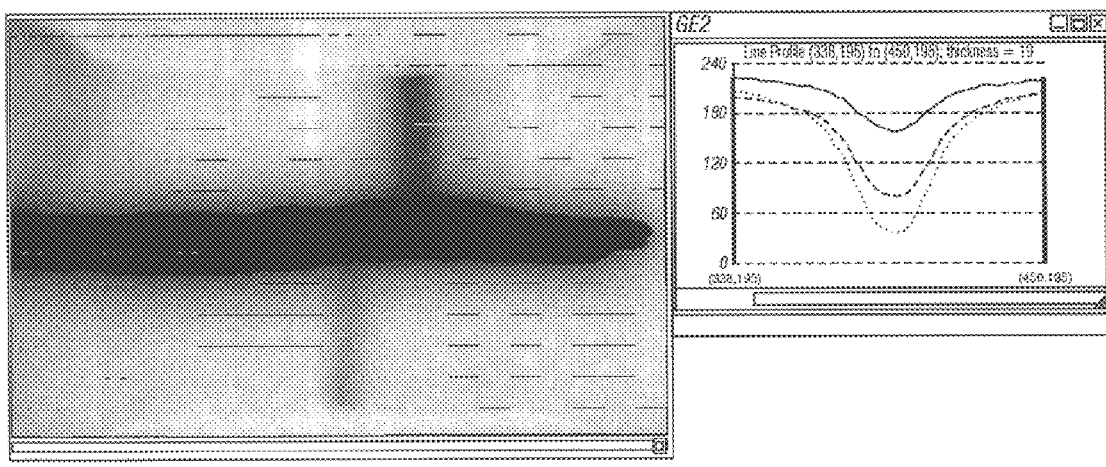
FIG. 8—Liquid reagent calibration system reaction line measurement. Glucose sample. concentration 74 mg/dL; glucose liquid calibrator concentration 2000 mg/dL.

Referring to FIG. 7, the liquid reagent calibrator system illustrates another embodiment of the present invention. Hydrophobic ink 70 was applied to the membrane separating the liquid calibrator 72 from the glucose analyte sample 74, forming a hydrophobic ink barrier. Liquid reagent was applied 71 and the calibrator interface 78 formed separately and distinctly from the reaction interface 76. Referring to FIG. 8, liquid Trinder reagent was introduced to the opposite side of the device and traveled around the ink track to meet the liquid calibrator and glucose sample at the interface. Hydrophobic ink may be used to contain and direct fluid flow.

Hydrophobic ink may be selected for its ability to segregate fluids and for its compatibility with the chemistry involved. Black ink from a Sharpie™ marker was used for this purpose, but was later suspected of interfering with the glucose chemistry. Membranes marked with hydrophobic ink are preferably incubated in a vacuum chamber for a time sufficient to evaporate any traces of solvents that may be present. Preferably, an incubation time of at least one hour should be used.

Example 4

Figure 9:
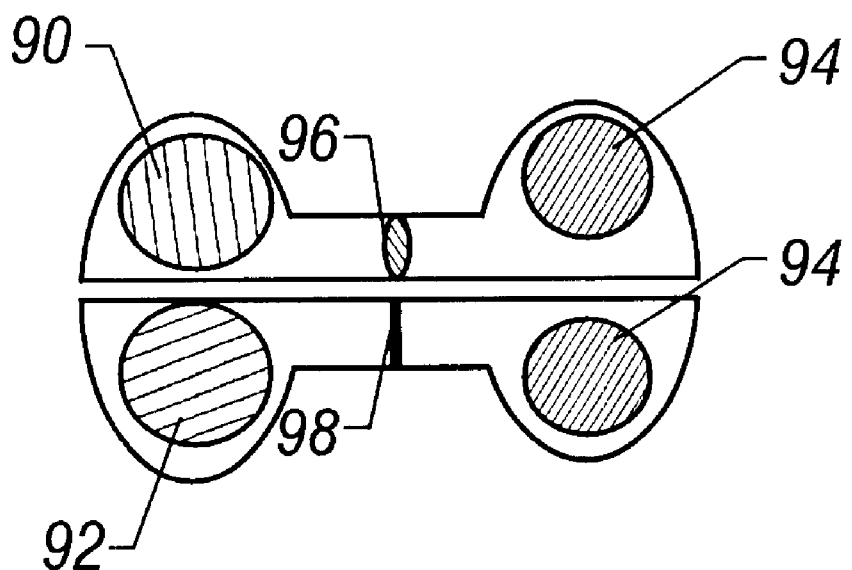
FIG. 9—Liquid reagent calibration system with split dogbone.

Referring to FIG. 9, this example illustrates an embodiment of the present invention using membranes in the shape of a "split dogbone" in an assay for glucose concentration. This embodiment was found to eliminate any interferences that may have been caused by the ink.

Figure 11:
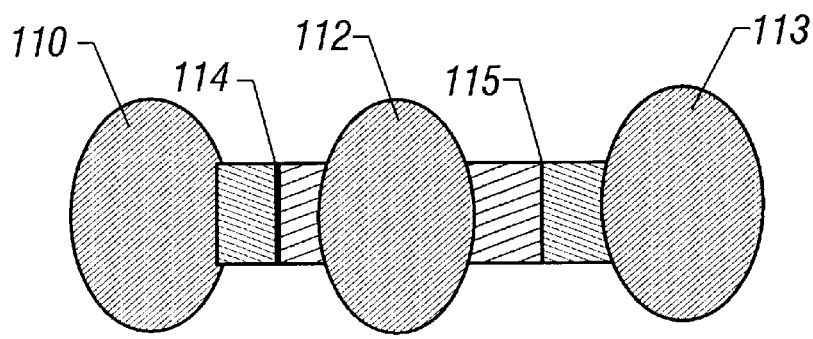
FIG. 11—Dried reagent calibration system using 3-ear dogbone format.

Membranes were dissected lengthwise to separate the liquid calibrator 90 from the liquid analyte sample 92. Calibrator and analyte samples (4 μl each) were applied to the membrane, and the assay was conducted as two synchronized devices. Reagent was applied 94 as two 4 μl aliquots on the top and bottom halves of one "dog-ear." The calibrator interface 96 formed separately from the reaction interface 98. Referring to Tables 6 and 7, this format facilitates corrections of sample slope and accurate prediction of analyte concentration. Table 7 presents data derived from ten different reagent preparations. These preparations were made using small random dilutions of reagent using water as diluent to arrive at ten reagent samples of slightly different and unknown concentrations. Other embodiments of the present invention are presented in FIG. 10 (dried calibrator 100 on split dogbone format). FIG. 10 shows the sites of application of liquid reagent 101, the calibrator interface 102, and the reaction interface 103. FIG. 11 shows a dried calibrator on 3-ear dogbone format. The sites of application of calibrator 110, reagent 112, and analyte sample 113 are indicated, as well as the calibrator interface 114, and reaction interface 115.

TABLE 6

Liquid reagent calibration system adjustment of assay results. Calibrator corrects for gross changes in reagent delivery (i.e. diluting reagent strength).

| Reagent Level | Uncorrected Dose | Corrected Dose |
|---|---|---|
| 173 mg/dL | | |
| 1X | 242.53 | 171.6 |
| 0.8X | 173.00 | 176.6 |
| 0.7X | 100.32 | 172.6 |
| 0.6X | 11.03 | 174.6 |
| Average | 131.72 | 173.8 |
| % CV | 75.33% | 1.23% |
| Actual | 173 | 173 |
| 267 mg/dL | | |
| 1X | 359.72 | 266.2 |
| 0.8X | 267.00 | 263.9 |
| 0.7X | 182.89 | 261.6 |
| 0.6X | 75.90 | 266.6 |
| Average | 221.38 | 264.6 |
| % CV | 54.62% | 1.30% |
| Actual | 267 | 267 |
| 362 mg/dL | | |
| 1X | 475.31 | 364.0 |
| 0.8X | 362.00 | 365.5 |
| 0.7X | 236.76 | 352.3 |
| 0.6X | 109.89 | 372.7 |
| Average | 295.99 | 363.6 |
| % CV | 53.30% | 2.28% |
| Actual | 362 | 362 |

TABLE 7

Liquid reagent calibration system corrects imprecision due to reagent variations.
171 mg/dL vs Random Reagent Ollusions

| 8/9/00 | Cal Slope y1 | Rxn Slope x1 | Adj Rxn Slope x0 |
|---|---|---|---|
| Curve 1 | 15.91 | 7.40 | 7.24 |
| Curve 2 | 13.54 | 5.97 | 6.66 |
| Curve 3 | 12.36 | 5.86 | 6.97 |
| Curve 4 | 13.52 | 6.35 | 7.05 |
| Curve 5 | 14.53 | 6.39 | 6.72 |
| Curve 6 | 12.34 | 5.81 | 6.93 |
| Curve 7 | 12.71 | 5.98 | 6.96 |
| Curve 8 | 14.57 | 6.59 | 6.91 |
| Curve 9 | 12.76 | 5.99 | 6.96 |
| Curve 10 | 16.40 | 7.14 | 6.81 |
| Mean | 13.88 | 6.35 | 6.92 |
| % CV | 10.50% | 8.65% | 2.38% |

Example 5

Figure 12:
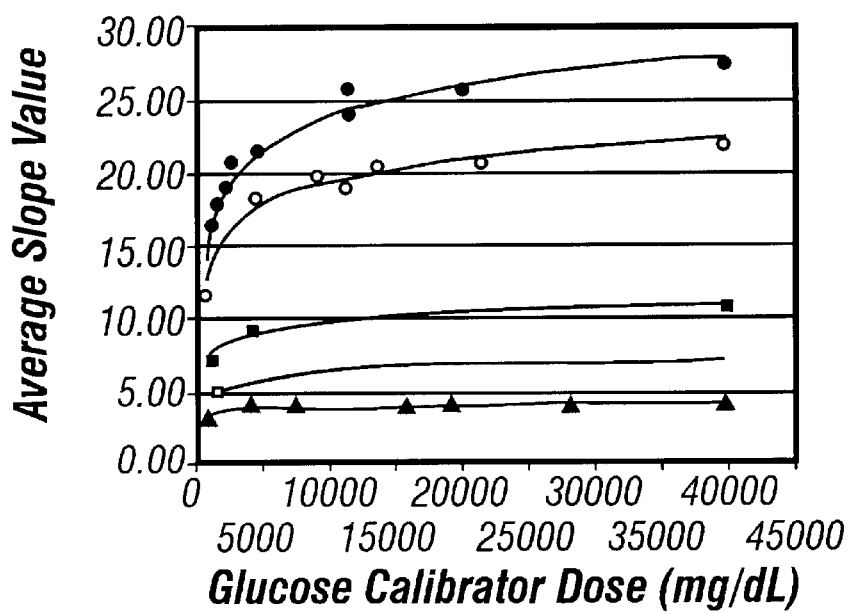
FIG. 12—Liquid reagent calibration system titration of calibrator.
Figure 12:
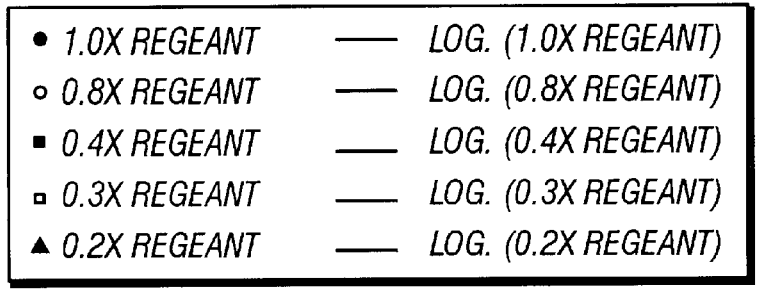
Figure 13:
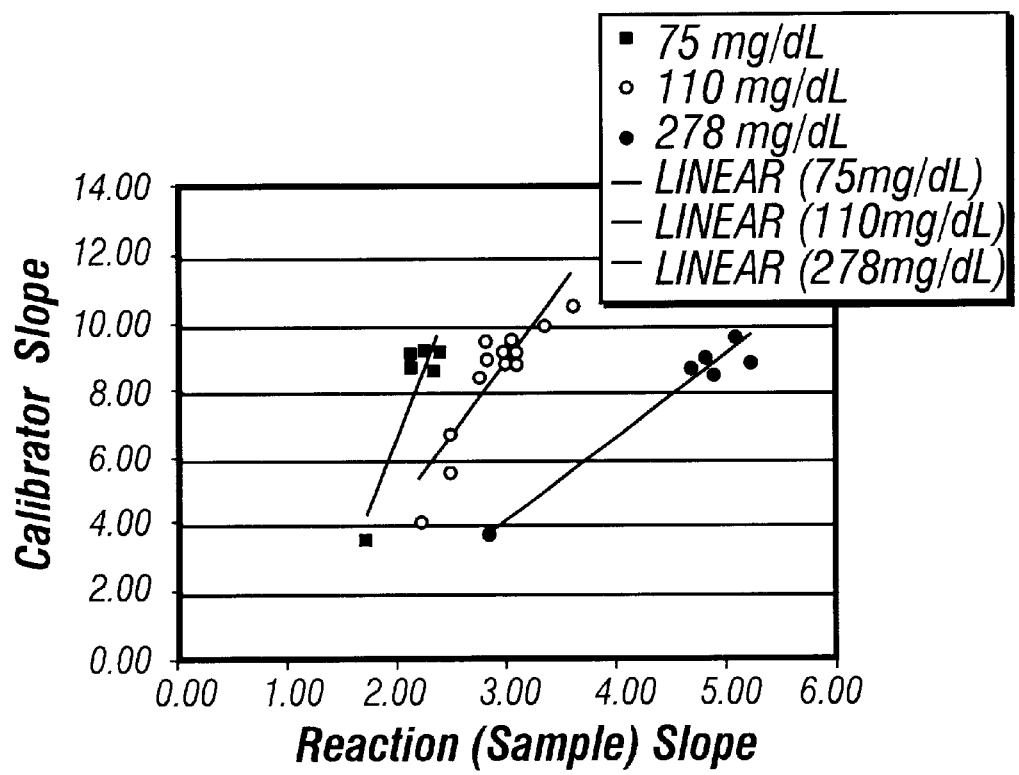
FIG. 13—Liquid reagent calibration system: "Real Life" calibrator fan.
Figure 14:
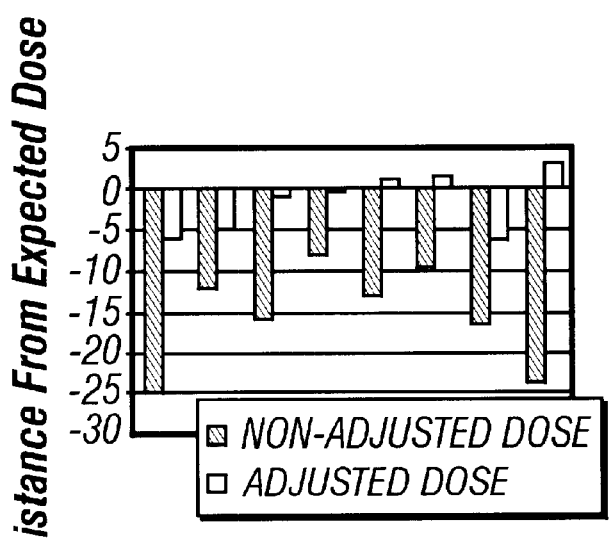
FIG. 14—Histogram analysis of "Real Life" fan corrections. The bar graphs shows non-adjusted concentration v. adjusted concentration by glucose calibrator, day 7 distance from expected concentration of 117.4.

Referring to FIG. 12, this example illustrates the preparation of a titration curve at five different reagent levels with glucose as the calibrator. Referring to FIG. 2, a calibrator that is in gross excess has a response that does not change meaningfully due to changes in calibrator concentration, as illustrated in the shaded Region of Interest. The titration curve of FIG. 12 indicates that calibrator excess conditions may not be achieved at the 1× reagent level. Therefore, calibrator systems may need to operate at lower reagent levels. In this embodiment, the liquid calibrator system for glucose utilized reagent strength of 0.4× (40%) of full strength commercially available Trinder reagent (from Sigma Chemical Co). The 1× reagent is formulated as follows: 5 mmol/L 4-aminoantipyrine, 200 mmol/L 3-5-dichloro-2-hydroxybenzenesulfonic acid, 75,000 U/L glucose oxidase, 50,000 U/L horseradish peroxidase, buffer at pH 7.0±0.1, and stabilizers and fillers.

The 0.4× reagent level provided a "gross excess" of calibrator within the Region of Interest depicted in FIG. 2, as well as was able to generate an assay response that varies with reagent concentration within the Region of Interest of FIG. 1. Table 8 illustrates that when the reagent is not in excess, fluctuations in calibrator concentration do not impact the calibrator reaction rate slope.

TABLE 8

Fluctuating the calibrator level. Minor fluctuations (+/−) in the calibrator concentration do not affect the overall calibrator slope.

| 13,200 mg/dL Calibrator with 109 mg/dL vs 0.4 × Reagent | | 13,200 mg/dL Calibrator with 381 mg/dL vs 0.4 × Reagent | |
|---|---|---|---|
| Cal | Rxn | Cal | Rxn |
| 1 = 10.47 | 3.47 | 1 = 10.2 | 6.09 |
| 2 = 10.54 | 3.45 | 2 = 10.12 | 5.85 |
| 3 = 10.23 | 3.73 | 3 = 10.39 | 6.11 |
| Average = 10.42 | 3.55 | Average = 10.24 | 6.02 |
| SD = 0.16 | 0.16 | SD = 0.14 | 0.14 |
| % CV = 1.56% | 4.37% | % CV = 1.38% | 2.40% |

| 14,700 mg/dL Calibrator with 109 mg/dL vs 0.4 × Reagent | | 14,700 mg/dL Calibrator with 381 mg/dL vs 0.4 × Reagent | |
|---|---|---|---|
| Cal | Rxn | Cal | Rxn |
| 1 = 10 | 3.46 | 1 = 9.92 | 6.26 |
| 2 = 10.26 | 3.37 | 2 = 9.86 | 6.33 |
| 3 = 9.71 | 3.28 | 3 = 10.38 | 6.24 |
| Average = 9.99 | 3.37 | Average = 10.05 | 6.28 |
| SD = 0.28 | 0.09 | SD = 0.28 | 0.04 |
| % CV = 2.79% | 2.66% | % CV = 2.83% | 0.71% |

| 18,100 mg/dL Calibrator with 109 mg/dL vs 0.4 × Reagent | | 18,100 mg/dL Calibrator with 381 mg/dL vs 0.4 × Reagent | |
|---|---|---|---|
| Cal | Rxn | Cal | Rxn |
| 1 = 10.13 | 3.36 | 1 = 10.63 | 6.08 |
| 2 = 10.04 | 3.42 | 2 = 10.18 | 6.02 |
| 3 = 10.88 | 3.43 | 3 = 10.61 | 6.3 |
| Average = 10.35 | 3.41 | Average = 10.47 | 6.13 |
| SD = 0.46 | 0.04 | SD = 0.25 | 0.14 |
| % CV = 4.42% | 1.09% | % CV = 2.41% | 2.34% |

Example 6

This example illustrates the present invention applied to determinations of glucose analyte concentrations over a period of two weeks. It is shown that accurate measurements were obtainable at the two week period.

This example followed the slope value relationship over two weeks, utilizing different camera stations, and working with 0.4× strength reagents stored at various temperatures. The slope value of the 110 mg/dL dose curve on the fan created in this example is 4.37. Note that the calibration fan of FIG. 3 has a similar value of 4.10. The method of the present invention was compared with the commercially available Trinder-based Vitros™ glucose assay for determining unknown glucose concentrations. Referring to Table 9, the average Vitros™ value obtained was 111 mg/dL. The measured (unadjusted) glucose concentration values ranged from 128.8 to 63.0, averaging 96.6 mg/dL and therefore differing by −12.8%. When adjusted according to the present invention, glucose concentrations ranged from 130.3 to 94.7 and averaged 112.9, differing by 1.95% from the Vitros™ average.

Table 10 shows unadjusted glucose concentration values ranging from 117.4 to 63.0, averaging 96.6 for a difference of −12.8%. Glucose values adjusted according to the calibrator system of the present invention ranged from 126.0 to 94.4 averaging 111.8 differing by 1.0% from the Vitros™ average. It is therefore apparent that the present invention functions well to produce accurate results over several days and various conditions to produce accurate and useful results. These results are of an accuracy comparable to that of established prior art methods but without the disadvantages of utilizing the prior art methods.

contacting the reagent with the analyte sample and the calibrator, wherein analyte sample and calibrator sample are applied to a solid phase and travel through the solid phase to form a reaction interface with the reagent;

mathematically relating a reaction measurement of the analyte sample with the reagent and a reaction measurement of the calibrator with the reagent as an equation defining a three-dimensional surface;

TABLE 9

Liquid Reagent Calibration System. Day-to-day adjustments using the original Calibrator Fan. "Dose" indicates analyte concentration.

| Day | Date | Storage Temp | Dose No Adj | Dose w/Adj | Vitros Value | No Adj % Diff from Vitros | w/Adj % Diff from Vitros |
|---|---|---|---|---|---|---|---|
| 1 | 8/16/00 | 4° C. | 117.36 | 117.36 | 110 | 6.69% | 6.69% |
| 3 | 8/18/00 | 4° C. | 88.59 | 106.11 | 110 | −19.46% | −3.54% |
| 5 | 8/21/00 AM | 4° C. | 128.77 | 121.87 | 118 | 9.13% | 3.28% |
| 5 | 8/21/00 PM | 4° C. | 103.82 | 113.39 | 118 | −12.02% | −3.90% |
| 6 | 8/22/00 AM | 4° C. | 98.55 | 107.67 | 111 | −11.22% | −3.00% |
| 6 | 8/22/00 PM | 4° C. | 102.00 | 115.40 | 111 | −8.11% | 3.97% |
| 7 | 8/23/00 | 4° C. | 102.72 | 107.99 | 111 | −7.46% | −2.71% |
| 7 | 8/23/00 | 22° C. | 102.17 | 110.30 | 111 | −7.96% | −0.63% |
| 7 | 8/23/00 | 37° C. | 89.38 | 94.71 | 111 | −19.47% | −14.67% |
| 8 | 8/24/00 | 4° C. | 98.56 | 110.70 | 106 | −7.02% | 4.44% |
| 8 | 8/24/00 | 22° C. | 91.46 | 102.71 | 106 | −13.72% | −3.11% |
| 8 | 8/24/00 | 37° C. | 75.16 | 111.62 | 106 | −29.09% | 5.30% |
| 9 | 8/25/00 | 22° C. | 104.64 | 118.20 | 108 | −3.11% | 9.44% |
| 9 | 8/25/00 | 37° C. | 76.08 | 125.98 | 108 | −29.55% | 16.65% |
| 12 | 8/28/00 | 22° C. | 102.94 | 111.62 | 111 | −7.26% | 0.55% |
| 12 | 8/28/00 | 37° C. | 62.95 | 130.31 | 111 | −43.29% | 17.39% |
| | Average | | 96.57 | 112.87 | 111 | −12.77% | 1.95% |
| | SD | | 16.09 | 8.78 | 4 | | |
| | % CV | | 16.66% | 7.78% | 3.69% | | |

TABLE 10

Day-to-day adjustments of the liquid reagent calibration. "Dose" indicates analyte concentration.

| Day | Date | Storage Temp | Dose No Adj | Dose w/Adj | Vitros Value | No Adj % Diff from Vitros | w/Adj % Diff from Vitros |
|---|---|---|---|---|---|---|---|
| 1 | 8/16/00 | 4° C. | 117.36 | 117.36 | 110 | 6.69% | 6.69% |
| 3 | 8/18/00 | 4° C. | 88.59 | 105.02 | 110 | −19.46% | −4.52% |
| 5 | 8/21/00 AM | 4° C. | 128.77 | 122.37 | 118 | 9.13% | 3.70% |
| 5 | 8/21/00 PM | 4° C. | 103.82 | 112.81 | 118 | −12.02% | −4.40% |
| 6 | 8/22/00 AM | 4° C. | 98.55 | 107.09 | 111 | −11.22% | −3.52% |
| 6 | 8/22/00 PM | 4° C. | 102.00 | 114.57 | 111 | −8.11% | 3.22% |
| 7 | 8/23/00 | 4° C. | 102.72 | 107.67 | 111 | −7.46% | −3.00% |
| 7 | 8/23/00 | 22° C. | 102.17 | 109.79 | 111 | −7.96% | −1.09% |
| 7 | 8/23/00 | 37° C. | 89.38 | 94.37 | 111 | −19.47% | −14.98% |
| 8 | 8/24/00 | 4° C. | 98.56 | 109.95 | 106 | −7.02% | 3.73% |
| 8 | 8/24/00 | 22° C. | 91.46 | 101.99 | 106 | −13.72% | −3.78% |
| 8 | 8/24/00 | 37° C. | 75.16 | 109.32 | 106 | −29.09% | 3.13% |
| 9 | 8/25/00 | 22° C. | 104.64 | 117.34 | 108 | −3.11% | 8.65% |
| 9 | 8/25/00 | 37° C. | 76.08 | 122.80 | 108 | −29.55% | 13.70% |
| 12 | 8/28/00 | 22° C. | 102.94 | 111.07 | 111 | −7.26% | 0.07% |
| 12 | 8/28/00 | 37° C. | 62.95 | 125.98 | 111 | −43.29% | 13.50% |
| | Average | | 96.57 | 111.84 | 111 | −12.77% | 1.02% |
| | SD | | 16.09 | 8.18 | 4 | | |
| | % CV | | 16.66% | 7.31% | 3.69% | | |

What is claimed is:

1. A method for the calibration of a detection and/or quantification assay for an analyte to be assayed for comprising, providing a reagent that provides a detectable signal after reacting with the analyte to be assayed for, wherein the reagent also provides a detectable signal after reacting with a calibrator;

utilizing the mathematical relationship to calibrate the detection and/or quantification assay.

2. The method of claim 1 wherein the reaction measurement of the calibrator is the slope of the line defining the reaction rate of the calibrator, and the reaction measurement of the analyte sample is the slope of the line defining the reaction rate of the analyte sample.

3. The method of claim 2 wherein the calibration and performance of the assay are simultaneous.

4. The method of claim 2 wherein the calibrator is provided in an amount defined by a region of interest.

5. The method of claim 1 wherein the calibrator is provided in excess of the concentration of the reagent.

6. The method of claim 5 wherein the calibrator is provided in an amount in gross excess to that of the reagent.

7. The method of claim 1 wherein the analyte is selected from the group consisting of alanine amino tranferase, albumin, alkaline phosphatase, ammonia, amylase, aspartate amino transferase, total bilirubin, calcium, cholesterol, creatine kinase, creatinine, 2-glutamyl transferase, glucose, lactate dehydrogenase, lipase, magnesium, phosphorus, protein, triglyceride, urea nitrogen, uric acid.

8. The method of claim 7 wherein the analyte is selected from the group consisting of: alanine amino transferase, cholesterol, glucose, and phosphorus.

9. The method of claim 1 wherein the calibrator is the same chemical as the analyte to be assayed for.

10. The method of claim 9 wherein the calibrator is provided in a concentration of at least 10 times the concentration of the analyte to be assayed for in the assay sample.

11. The method of claim 1 wherein the calibrator is an analog of the analyte to be assayed for.

12. The method of claim 1 wherein the mathematical relationship relates the slope of the line defining the reaction rate of the analyte with the reagent and the slope of the line defining the reaction rate of the calibrator with the reagent.

13. The method of claim 1 wherein the mathematical relationship is an algorithm.

14. The method of claim 1 wherein the mathematical relationship is selected from the group consisting of: fourier series bivariate, cosine series bivariate, sigmoid series bivariate, Chebyshev x,y bivariate polynomial, Chebyshev X, LnY bivariate polynomial, Chebyshev LnX, Y bivariate polynomial, Chebyshev LnX, LnY bivariate polynomial, Taylor series rational, and Chebyshev series rational.

15. The method of claim 14 wherein the mathematical relationship is a Chebyshev X, LnY bivariate polynomial.

16. The method of claim 15 wherein the Chebyshev X, LnY bivariate polynomial is a Chebyshev X, LnY bivariate polynomial Order 6 equation.

17. The method of claim 1 comprised in a dry chemistry format comprising a solid phase charged with a reagent.

18. The method of claim 1 in a liquid chemistry format.

19. The method of claim 17 further comprising that:
a reagent is charged on the solid phase;
a diluent is applied to the solid phase; and
the diluent travels through the solid phase and dissolves the reagent charged on the solid phase.

20. The method of claim 19 wherein at least two of the analyte sample, calibrator sample, and reagent are applied to the solid phase at separate and distinct points.

21. The method of claim 19 wherein the analyte sample, calibrator sample, and reagent travel through the solid phase;
the analyte sample and reagent form a first reaction interface; and
the calibrator sample and reagent form a reaction interface that is separate and distinct from the first reaction interface.

22. A method for the calibration of a detection and/or quantification assay for an analyte comprising,
providing a reagent that provides a detectable signal when an analyte to be assayed for is present in an assay sample;
providing a calibrator that provides a detectable signal when an analyte to be assayed for is present in an assay sample;
contacting the reagent with the analyte sample and the calibrator, wherein the analyte sample and the calibrator sample are applied to a solid phase and travel through the solid phase to form a reaction interface with the reagent;
determining the slope of the line defining the reaction rate of the reagent with the analyte to be assayed for;
determining the slope of the line defining the reaction rate of the reagent with the calibrator;
providing a mathematical relationship between the slope of the line defining the reaction rate of the reagent with the analyte to be assayed for and the slope of the line defining the reaction rate of the reagent with the calibrator;
utilizing the mathematical relationship to determine the presence or concentration of the analyte in the sample of the analyte.

23. The method of claim 22 further comprising constructing a calibration fan from the slope of the lines defining the reaction rate of the analyte to be assayed for at different reagent concentrations, and the slope of the lines defining the reaction rate of the calibrator with the reagent at different reagent concentrations.

24. The method of claim 23 wherein the calibration and performance of the assay are simultaneous.

25. The method of claim 22 wherein the mathematical relationship is represented by an analyte fan curve.

26. The method of claim 25 wherein two axes of the analyte fan curve are the analyte concentration and calibrator fan slope.

27. The method of claim 22 wherein measurements of the slope of the line defining the reaction rate of the reagent with the analyte sample and the slope of the line defining the reaction rate of the reagent with the calibrator define an (x,y) pair on the calibration fan.

28. The method of claim 22 wherein the concentration of analyte in the sample is determined by identifying on the calibration fan the intersection of the slope of the line defining the reaction rate of the analyte sample and the slope of the line defining the reaction rate of the calibrator.

29. The method of claim 22 wherein the calibrator is provided in excess of the concentration of the reagent.

30. The method of claim 29 wherein the calibrator is provided in an amount in gross excess to that of the reagent.

31. The method of claim 22 wherein the analyte is selected from the group consisting of: alanine amino tranferase, albumin, alkaline phosphatase, ammonia, amylase, aspartate amino transferase, total bilirubin, calcium, cholesterol, creatine kinase, creatinine, 2-glutamyl transferase, glucose, lactate dehydrogenase, lipase, magnesium, phosphorus, protein, triglyceride, urea nitrogen, uric acid.

32. The method of claim 31 wherein the analyte is selected from the group consisting of: alanine amino transferase, cholesterol, glucose, and phosphorus.

33. The method of claim 22 wherein the calibrator is provided in an amount defined by a region of interest.

34. The method of claim 22 wherein the calibrator is the same chemical as the analyte to be assayed for.

35. The method of claim 34 wherein the calibrator is provided in a concentration of at least 10 times the concentration of the analyte to be assayed for in the assay sample.

36. The method of claim 22 wherein the calibrator is an analog of the analyte to be assayed for.

37. The method of claim 22 comprised in a dry chemistry format comprising a solid phase charged with a reagent.

38. The method of claim 37, further comprising that the analyte sample and calibrator sample are applied to the solid phase and travel through the solid phase to form a reaction interface with the reagent.

39. The method of claim 38 wherein at least two of the analyte sample, calibrator sample, and reagent are applied to the solid phase at separate and distinct points.

40. The method of claim 38 wherein the analyte sample, calibrator sample, and reagent travel through the solid phase;
   the analyte sample and reagent form a first reaction interface; and
   the calibrator sample and reagent form a reaction interface that is separate and distinct from the first reaction interface.

41. The method of claim 37 further comprising that:
   a reagent is charged on the solid phase;
   a diluent is applied to the solid phase; and
   the diluent travels through the solid phase and dissolves the reagent charged on the solid phase.

42. The method of claim 22 in a liquid chemistry format.

43. A method for performing a detection and/or quantification assay comprising:
   providing a sample suspected of containing an analyte;
   providing a reagent that produces a detectable signal after reacting with the analyte;
   providing a gross excess of a calibrator that produces a detectable signal after reacting with the reagent;
   contacting the reagent with the analyte sample and the calibrator;
   mathematically relating a reaction measurement of the sample analyte with the reagent and a reaction measurement of the calibrator with the reagent as an equation defining a three-dimensional surface; and
   utilizing the mathematical relationship to calibrate the detection and/or quantification assay,
   wherein the step of providing a gross excess of a calibrator serves to ensure there is no meaningful effect on the assay results due to variations in delivery of calibrator to the reaction.

44. The method of claim 43 wherein the reaction measurement of the calibrator is the slope of the line defining the reaction rate of the calibrator, and the reaction measurement of the analyte sample is the slope of the line defining the reaction rate of the analyte sample.

45. The method of claim 43 wherein the analyte is selected from the group consisting of: alanine amino transferase, albumin, alkaline phosphatase, ammonia, amylase, aspartate amino transferase, total bilirubin, calcium, cholesterol, creatine kinase, creatinine, 2-glutamyl transferase, glucose, lactate dehydrogenase, lipase, magnesium, phosphorus, protein, triglyceride, urea nitrogen, and uric acid.

46. The method of claim 45 wherein the analyte is selected from the group consisting of: alanine amino transferase, cholesterol, glucose, and phosphorus.

47. The method of claim 43 wherein the calibration and performance of the assay are simultaneous.

48. The method of claim 43 wherein the calibrator is provided in an amount defined by a region of interest.

49. The method of claim 43 wherein the calibrator is the same chemical as the analyte to be assayed for.

50. The method of claim 49 wherein the calibrator is provided in a concentration of at least 10 times the concentration of the analyte to be assayed for in the assay sample.

51. The method of claim 43 wherein the calibrator is an analog of the analyte to be assayed for.

52. The method of claim 43 wherein the mathematical relationship relates the slope of the line defining the reaction rate of the analyte with the reagent and the slope of the line defining the reaction rate of the calibrator with the reagent.

53. The method of claim 43 wherein the mathematical relationship is an algorithm.

54. A The method of claim 43 wherein the mathematical relationship is selected from the group consisting of: fourier series bivariate, cosine series bivariate, sigmoid series bivariate, Chebyshev x,y bivariate polynomial, Chebyshev X, LnY bivariate polynomial, Chebyshev LnX, Y bivariate polynomial, Chebyshev LnX, LnY bivariate polynomial, Taylor series rational, and Chebyshev series rational.

55. The method of claim 54 wherein the mathematical relationship is a Chebyshev X, LnY bivariate polynomial.

56. The method of claim 55 wherein the Chebyshev X, LnY bivariate polynomial is a Chebyshev X, LnY bivariate polynomial Order 6 equation.

57. The method of claim 43 comprised in a dry chemistry format comprising a solid phase charged with a reagent.

58. The method of claim 57, further comprising that the analyte sample and calibrator sample are applied to the solid phase and travel through the solid phase to form a reaction interface with the reagent.

59. The method of claim 57 further comprising that:
   a reagent is charged on the solid phase;
   a diluent is applied to the solid phase; and
   the diluent travels through the solid phase and dissolves the reagent charged on the solid phase.

60. The method of claim 59 wherein at least two of the analyte sample, calibrator sample, and reagent are applied to the solid phase at separate and distinct points.

61. The method of claim 59 wherein the analyte sample, calibrator sample, and reagent travel through the solid phase;
   the analyte sample and reagent form a first reaction interface; and
   the calibrator sample and reagent form a reaction interface that is separate and distinct from the first reaction interface.

62. The method of claim 43 in a liquid chemistry format.

* * * * *